(12) United States Patent
Den Boef et al.

(10) Patent No.: US 8,760,662 B2
(45) Date of Patent: Jun. 24, 2014

(54) METHOD AND APPARATUS FOR ANGULAR-RESOLVED SPECTROSCOPIC LITHOGRAPHY CHARACTERIZATION

(71) Applicant: ASML Netherlands B.V., Veldhoven (NL)

(72) Inventors: Arie Jeffrey Den Boef, Waalre (NL); Arno Jan Bleeker, Westerhoven (NL); Youri Johannes Laurentius Maria Van Dommelen, Eindhoven (NL); Mircea Dusa, Campbell, CA (US); Antoine Gaston Marie Kiers, Veldhoven (NL); Paul Frank Luehrmann, Sante Fe, NM (US); Henricus Petrus Maria Pellemans, Veldhoven (NL); Maurits Van Der Schaar, Veldhoven (NL); Cédric Désiré Grouwstra, Eindhoven (NL); Markus Gerardus Martinus Maria Van Kraaij, Mierlo (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 14/011,663

(22) Filed: Aug. 27, 2013

(65) Prior Publication Data
US 2014/0055788 A1 Feb. 27, 2014

Related U.S. Application Data

(60) Division of application No. 13/249,566, filed on Sep. 30, 2011, now Pat. No. 8,553,230, which is a continuation of application No. 12/805,852, filed on Aug. 20, 2010, now Pat. No. 8,054,467, which is a continuation of application No. 11/203,418, filed on Aug. 15, 2005, now Pat. No. 7,791,732, which is a continuation-in-part of application No. 10/918,742, filed on Aug. 16, 2004, now Pat. No. 7,791,727.

(51) Int. Cl.
*G01J 3/45* (2006.01)

(52) U.S. Cl.
USPC .......................................... 356/456

(58) Field of Classification Search
USPC .................. 356/456, 494, 511, 521
See application file for complete search history.

(56) References Cited

U.S. PATENT DOCUMENTS 3,909,602 A 9/1975 Micka
4,236,823 A * 12/1980 Roach et al. .................. 356/521

(Continued)

FOREIGN PATENT DOCUMENTS

EP 0 396 409 B1 11/1990
EP 0 882 976 A1 12/1998

(Continued)

OTHER PUBLICATIONS

English-Language Abstract for Japanese Patent Publication No. 01-303721 A, published Dec. 7, 1989; 1 page.

(Continued)

*Primary Examiner* — Tarifur Chowdhury
*Assistant Examiner* — Jonathon Cook
(74) *Attorney, Agent, or Firm* — Sterne, Kessler, Goldstein & Fox P.L.L.C.

(57) ABSTRACT

An apparatus and method to determine a property of a substrate by measuring, in the pupil plane of a high numerical aperture lens, an angle-resolved spectrum as a result of radiation being reflected off the substrate. The property may be angle and wavelength dependent and may include the intensity of TM- and TE-polarized radiation and their relative phase difference.

7 Claims, 13 Drawing Sheets

(56) References Cited

U.S. PATENT DOCUMENTS

| | | | |
|---|---|---|---|
| 4,538,914 | A | 9/1985 | Yomoda et al. |
| 4,672,196 | A | 6/1987 | Canino |
| 4,999,014 | A | 3/1991 | Gold et al. |
| 5,042,951 | A | 8/1991 | Gold et al. |
| 5,106,196 | A | 4/1992 | Brierley |
| 5,153,669 | A | 10/1992 | DeGroot |
| 5,166,752 | A | 11/1992 | Spanier et al. |
| 5,192,980 | A | 3/1993 | Dixon et al. |
| 5,218,415 | A | 6/1993 | Kawashima |
| 5,349,440 | A | 9/1994 | DeGroot |
| 5,412,473 | A | 5/1995 | Rosencwaig et al. |
| 5,541,731 | A | 7/1996 | Freedenberg et al. |
| 5,596,411 | A | 1/1997 | Fanton et al. |
| 5,703,692 | A | 12/1997 | McNeil et al. |
| 5,713,364 | A | 2/1998 | DeBaryshe et al. |
| 5,747,813 | A | 5/1998 | Norton et al. |
| 5,771,094 | A | 6/1998 | Carter et al. |
| 5,877,859 | A | 3/1999 | Aspnes et al. |
| 5,880,838 | A | 3/1999 | Marx et al. |
| 5,910,842 | A | 6/1999 | Piwonka-Corle et al. |
| 5,963,329 | A | 10/1999 | Conrad et al. |
| 6,078,380 | A | 6/2000 | Taniguchi et al. |
| 6,080,990 | A | 6/2000 | Watanabe et al. |
| 6,122,051 | A | 9/2000 | Ansley et al. |
| 6,177,994 | B1 | 1/2001 | Watson et al. |
| 6,417,916 | B1 | 7/2002 | Dengler et al. |
| 6,429,930 | B1 | 8/2002 | Littau et al. |
| 6,429,943 | B1 | 8/2002 | Opsal et al. |
| 6,449,037 | B2 | 9/2002 | Jun et al. |
| 6,515,744 | B2 | 2/2003 | Wei |
| 6,532,076 | B1 | 3/2003 | Sidorowich |
| 6,606,152 | B2 | 8/2003 | Littau et al. |
| 6,608,690 | B2 | 8/2003 | Niu et al. |
| 6,654,131 | B2 | 11/2003 | Opsal et al. |
| 6,699,624 | B2 | 3/2004 | Niu et al. |
| 6,704,661 | B1 | 3/2004 | Opsal et al. |
| 6,710,876 | B1 | 3/2004 | Nikoonahad et al. |
| 6,721,691 | B2 | 4/2004 | Bao et al. |
| 6,738,138 | B2 | 5/2004 | Wei |
| 6,750,968 | B2 | 6/2004 | Sandusky |
| 6,753,961 | B1 | 6/2004 | Norton et al. |
| 6,762,111 | B2 | 7/2004 | Fukuda |
| 6,768,983 | B1 | 7/2004 | Jakatdar et al. |
| 6,772,084 | B2 | 8/2004 | Bischoff et al. |
| 6,775,015 | B2 | 8/2004 | Bischoff et al. |
| 6,778,911 | B2 | 8/2004 | Opsal et al. |
| 6,781,706 | B2 | 8/2004 | Sidorowich |
| 6,785,638 | B2 | 8/2004 | Niu et al. |
| 6,791,679 | B2 | 9/2004 | Engelhard et al. |
| 6,804,005 | B2 | 10/2004 | Bischoff et al. |
| 6,813,034 | B2 | 11/2004 | Rosencwaig et al. |
| 6,819,426 | B2 | 11/2004 | Sezginer et al. |
| 6,829,057 | B2 | 12/2004 | Opsal et al. |
| 6,842,259 | B2 | 1/2005 | Rosencwaig et al. |
| 6,856,408 | B2 | 2/2005 | Raymond |
| 6,866,153 | B2 | 3/2005 | Turner, Jr. et al. |
| 6,870,621 | B2 | 3/2005 | Wei |
| 6,885,464 | B1 | 4/2005 | Pfeiffer et al. |
| 6,886,153 | B1 | 4/2005 | Bevis |
| 6,919,964 | B2 | 7/2005 | Chu |
| 6,921,916 | B2 | 7/2005 | Adel et al. |
| 6,928,628 | B2 | 8/2005 | Seligson et al. |
| 6,931,361 | B2 | 8/2005 | Opsal et al. |
| 6,947,850 | B2 | 9/2005 | Opsal et al. |
| 6,949,462 | B1 | 9/2005 | Yang et al. |
| 6,952,261 | B2 | 10/2005 | Ebert et al. |
| 6,972,852 | B2 | 12/2005 | Opsal et al. |
| 6,974,962 | B2 | 12/2005 | Brill et al. |
| 6,982,793 | B1 | 1/2006 | Yang et al. |
| 6,985,229 | B2 | 1/2006 | Lee et al. |
| 6,987,572 | B2 | 1/2006 | Lakkapragada et al. |
| 6,992,764 | B1 | 1/2006 | Yang et al. |
| 7,046,376 | B2 | 5/2006 | Sezginer |
| 7,061,615 | B1 | 6/2006 | Lowe-Webb |
| 7,061,622 | B2 | 6/2006 | Rollins et al. |
| 7,061,623 | B2 | 6/2006 | Davidson |
| 7,061,627 | B2 | 6/2006 | Opsal et al. |
| 7,068,363 | B2 | 6/2006 | Bevis et al. |
| 7,080,330 | B1 | 7/2006 | Choo et al. |
| 7,089,164 | B2 | 8/2006 | Middlebrooks |
| 7,112,813 | B2 | 9/2006 | Den Boef et al. |
| 7,115,858 | B1 | 10/2006 | Holden et al. |
| 7,139,081 | B2 | 11/2006 | De Groot |
| 7,148,959 | B2 | 12/2006 | Dusa et al. |
| 7,215,431 | B2 | 5/2007 | Opsal |
| 7,224,456 | B1 | 5/2007 | Phan et al. |
| 7,230,703 | B2 | 6/2007 | Sezginer et al. |
| 7,236,244 | B1 | 6/2007 | Yang et al. |
| 7,265,850 | B2 | 9/2007 | Archie et al. |
| 7,277,172 | B2 | 10/2007 | Kandel et al. |
| 7,280,212 | B2 | 10/2007 | Mieher et al. |
| 7,292,341 | B2 | 11/2007 | Brill et al. |
| 7,298,481 | B2 | 11/2007 | Mieher et al. |
| 7,301,649 | B2 | 11/2007 | Fabrikant et al. |
| 7,317,531 | B2 | 1/2008 | Mieher et al. |
| 7,333,200 | B2 | 2/2008 | Sezginer et al. |
| 7,365,858 | B2 | 4/2008 | Fang-Yen et al. |
| 7,440,105 | B2 | 10/2008 | Adel et al. |
| 7,483,133 | B2 | 1/2009 | Bareket et al. |
| 7,532,305 | B2 | 5/2009 | Den Boef et al. |
| 7,532,317 | B2 | 5/2009 | Smith et al. |
| 7,564,555 | B2 | 7/2009 | Den Boef et al. |
| 7,791,727 | B2 | 9/2010 | Den Boef et al. |
| 7,791,732 | B2 | 9/2010 | Den Boef et al. |
| 7,869,057 | B2 | 1/2011 | De Groot |
| 8,054,467 | B2 | 11/2011 | Den Boef et al. |
| 8,111,398 | B2 | 2/2012 | Van der Schaar et al. |
| 8,553,230 | B2 | 10/2013 | Den Boef et al. |
| 2002/0018217 | A1 | 2/2002 | Weber-Grabau et al. |
| 2002/0039184 | A1* | 4/2002 | Sandusky ............ 356/369 |
| 2002/0165636 | A1 | 11/2002 | Hasan |
| 2002/0166982 | A1 | 11/2002 | Kataoka et al. |
| 2002/0192577 | A1 | 12/2002 | Fay et al. |
| 2003/0002043 | A1 | 1/2003 | Abdulhalim et al. |
| 2003/0081216 | A1 | 5/2003 | Ebert et al. |
| 2003/0133102 | A1 | 7/2003 | Opsal |
| 2003/0143761 | A1 | 7/2003 | Fukuda |
| 2003/0163295 | A1 | 8/2003 | Jakatdar et al. |
| 2003/0225535 | A1 | 12/2003 | Doddi et al. |
| 2004/0004726 | A1 | 1/2004 | Sezginer et al. |
| 2004/0017574 | A1 | 1/2004 | Vuong et al. |
| 2004/0066517 | A1 | 4/2004 | Huang et al. |
| 2004/0070772 | A1 | 4/2004 | Shchegrov et al. |
| 2004/0078173 | A1 | 4/2004 | Bischoff et al. |
| 2004/0119970 | A1 | 6/2004 | Dusa et al. |
| 2004/0129900 | A1 | 7/2004 | Den Boef et al. |
| 2004/0133362 | A1 | 7/2004 | Barouch et al. |
| 2004/0167754 | A1 | 8/2004 | Bischoff et al. |
| 2004/0181768 | A1 | 9/2004 | Krukar |
| 2004/0189993 | A1 | 9/2004 | Ebert |
| 2004/0190008 | A1 | 9/2004 | Mieher et al. |
| 2004/0196460 | A1 | 10/2004 | Dobschal et al. |
| 2004/0201836 | A1 | 10/2004 | Chang et al. |
| 2004/0223137 | A1 | 11/2004 | Littau et al. |
| 2004/0239954 | A1 | 12/2004 | Bischoff |
| 2004/0246476 | A1 | 12/2004 | Bevis et al. |
| 2005/0012928 | A1 | 1/2005 | Sezginer et al. |
| 2005/0041258 | A1 | 2/2005 | Opsal et al. |
| 2005/0046855 | A1 | 3/2005 | Davidson |
| 2005/0106479 | A1 | 5/2005 | Geh et al. |
| 2005/0122516 | A1 | 6/2005 | Sezginer et al. |
| 2005/0123844 | A1 | 6/2005 | Monshouwer |
| 2005/0195412 | A1 | 9/2005 | Opsal |
| 2005/0209816 | A1 | 9/2005 | Vuong et al. |
| 2006/0007446 | A1 | 1/2006 | Boef et al. |
| 2006/0033921 | A1 | 2/2006 | Den Boef et al. |
| 2006/0066855 | A1 | 3/2006 | Boef et al. |
| 2006/0082792 | A1 | 4/2006 | Sezginer |
| 2006/0117293 | A1 | 6/2006 | Smith et al. |
| 2006/0126074 | A1 | 6/2006 | Van Der Werf et al. |
| 2006/0139592 | A1 | 6/2006 | Den Boef et al. |
| 2006/0243912 | A1 | 11/2006 | Raymond et al. |
| 2006/0250597 | A1 | 11/2006 | Nakajima |
| 2007/0019171 | A1 | 1/2007 | Smith |

(56) References Cited

U.S. PATENT DOCUMENTS

| | | |
|---|---|---|
| 2008/0036984 A1 | 2/2008 | Mos et al. |
| 2008/0043239 A1 | 2/2008 | Boef et al. |
| 2008/0074666 A1 | 3/2008 | Boef et al. |
| 2008/0144036 A1 | 6/2008 | Schaar |
| 2008/0158564 A1 | 7/2008 | Archie et al. |
| 2008/0239318 A1 | 10/2008 | Den Boef et al. |
| 2008/0311344 A1 | 12/2008 | Marie Kiers et al. |
| 2010/0277706 A1 | 11/2010 | Van der Schaar et al. |
| 2011/0007314 A1 | 1/2011 | Den Boef et al. |
| 2012/0038929 A1 | 2/2012 | Den Boef et al. |

FOREIGN PATENT DOCUMENTS

| | | |
|---|---|---|
| EP | 0 973 069 A2 | 1/2000 |
| EP | 1 400 855 A2 | 3/2004 |
| JP | 01-303721 A | 12/1989 |
| JP | 09-504861 A | 5/1997 |
| JP | 2000-097841 A | 4/2000 |
| JP | 2003-224057 A | 8/2003 |
| JP | 2004-287400 A | 10/2004 |
| JP | 2006-060214 A | 3/2006 |
| JP | 2006-157023 A | 6/2006 |
| JP | 2006-226994 A | 8/2006 |
| JP | 2006-518942 A | 8/2006 |
| JP | 2007-527531 A | 9/2007 |
| JP | 2008-542790 A | 11/2008 |
| WO | WO 95/02814 A1 | 1/1995 |
| WO | WO 03/065119 A2 | 8/2003 |
| WO | WO 03/075042 A2 | 9/2003 |
| WO | WO 2004/024328 A1 | 3/2004 |
| WO | WO 2004/053426 A1 | 6/2004 |
| WO | WO 2004/107415 A1 | 12/2004 |
| WO | WO 2005/028992 A2 | 3/2005 |
| WO | WO 2005/069082 A1 | 7/2005 |

OTHER PUBLICATIONS

English-Language Abstract for Japanese Patent Publication No. 2000-097841 A, published Apr. 7, 2000; 1 page.
English-Language Abstract for Japanese Patent Publication No. 2003-244507 A, published Aug. 29, 2003; 1 page.
English-Language Abstract for Japanese Patent Publication No. 2004-287400 A, published Oct. 14, 2004; 1 page.
English-Language Abstract for Japanese Patent Publication No. 2006-060214 A, published Mar. 2, 2006; 1 page.
English-Language Abstract for Japanese Patent Publication No. 2006-157023 A, published Jun. 15, 2006; 1 page.
English-Language Abstract for Japanese Patent Publication No. 2006-226994 A, published Aug. 31, 2006; 2 pages.
English-Language Abstract for Japanese Patent Publication No. 9-504861 A, published May 13, 1998; 1 page.
English-Language Translation of Notice of Reasons for Rejection directed to related Japanese Patent Application No. 2007-320546, mailed Jan. 14, 2011, from the Japanese Patent Office; 3 pages.
English-Language Translation of Notice of Reasons for Rejection directed to related Japanese Patent Application No. 2005-235188, mailed Mar. 3, 2009; 4 pages.
European Search Report issued for European Patent Application No. 05254994.6, dated Dec. 9, 2005.
European Search Report issued for European Patent Application No. 05254994.6-2222, dated Feb. 23, 2006.
"Interferometric Method of Checking the Overlay Accuracy in Photolithographic Exposure Processes," IBM Technical Disclosure Bulletin, vol. 32, No. 10B, IBM Corp., Mar. 1990; pp. 214-217.
"Inteferometric Measurement System for Overlay Measurement in Lithographic Processes," IBM Technical Disclosure Bulletin, vol.37, No. 02B, IBM Corp., Feb. 1994; pp. 535-536.
J. Bischoff et al., "Light Diffraction Based Overlay Measurement," Metrology, Inspection, and Process Control for Microlithography XV, vol. 4344, Proceedings of SPIE, 2001; pp. 222-223.
Krukar, R., "Overlay and Grating Line Shape Metrology Using Optical Scatterometry: Final Report," Defense Advanced Research Projects Agency (DOD), ARPA Order No. 5916, Nov. 20, 2001; 40 pages.
Naqvi, S.S.H., et al., "Diffractive techniques for lithographic process monitoring and control," J. Vac. Sci. Technol. B, vol. 12, No. 6, American Vacuum Society, 1994; pp. 3600-3606.
Zaidi, S.H., et al., "Moiré interferometric alignment and overlay techniques," SPIE vol. 2196, Center for High Technology Materials, University of New Mexico, 1994; pp. 371-381.
Non-Final Rejection mailed Feb. 9, 2007 for U.S. Appl. No. 10/918,742, filed Aug. 16, 2004; 30 pages.
Non-Final Rejection mailed Sep. 11, 2007 for U.S. Appl. No. 10/918,742, filed Aug. 16, 2004; 24 pages.
Final Rejection mailed Jun. 16, 2008 for U.S. Appl. No. 10/918,742, filed Aug. 16, 2004; 27 pages.
Non-Final Rejection mailed Nov. 10, 2008 for U.S. Appl. No. 10/918,742, filed Aug. 16, 2004; 18 pages.
Final Rejection mailed Apr. 29, 2009 for U.S. Appl. No. 10/918,742, filed Aug. 16, 2004; 14 pages.
Non-Final Rejection mailed Oct. 1, 2009 for U.S. Appl. No. 10/918,742, filed Aug. 16, 2004; 6 pages.
Notice of Allowance mailed Feb. 5, 2010 for U.S. Appl. No. 10/918,742, filed Aug. 16, 2004; 6 pages.
Notice of Allowance dated Jun. 11, 2010 for U.S. Appl. No. 10/918,742, filed Aug. 16, 2004; 6 pages.
Non-Final Rejection mailed Jun. 20, 2008 for U.S. Appl. No. 11/203,418, filed Aug. 15, 2005; 22 pages.
Final Rejection mailed Apr. 15, 2009 for U.S. Appl. No. 11/203,418, filed Aug. 15, 2005; 13 pages.
Non-Final Rejection mailed Sep. 2, 2009 for U.S. Appl. No. 11/203,418, filed Aug. 15, 2005; 14 pages.
Notice of Allowance mailed Feb. 3, 2010 for U.S. Appl. No. 11/203,418, filed Aug. 15, 2005; 10 pages.
Notice of Allowance mailed Jun. 24, 2010 for U.S. Appl. No. 11/203,418, filed Aug. 15, 2005; 6 pages.
Non-Final Rejection mailed Feb. 24, 2011 for U.S. Appl. No. 12/805,852, filed Aug. 20, 2010; 23 pages.
Notice of Allowance mailed Jun. 15, 2011 for U.S. Appl. No. 12/805,852, filed Aug. 20, 2010; 7 pages.
Notice of Allowance mailed Aug. 4, 2011 for U.S. Appl. No. 12/805,852, filed Aug. 20, 2010; 7 pages.
Non-Final Rejection mailed Nov. 7, 2012 for U.S. Appl. No. 13/249,566, filed Sep. 30, 2011; 12 pages.
Notice of Allowance mailed May 29, 2013 for U.S. Appl. No. 13/249/566, filed Sep. 30, 2011; 9 pages.
Non-Final Rejection mailed Jun. 12, 2008 for U.S. Appl. No. 11/641,124, filed Dec. 19, 2006; 19 pages.
Final Rejection mailed mailed Mar. 16, 2009 for U.S. Appl. No. 11/641,124, filed Dec. 19, 2006; 22 pages.
Non-Final Rejection mailed Jul. 21, 2009 for U.S. Appl. No. 11/641,124, filed Dec. 19, 2006; 23 pages.
Final Rejection mailed Jan. 29, 2010 for U.S. Appl. No. 11/641,124, filed Dec. 19, 2006; 26 pages.
Non-Final Rejection mailed Sep. 29, 2010 for U.S. Appl. No. 12/770,153, filed Apr. 29, 2010; 24 pages.
Non-Final Rejection mailed Apr. 28, 2011 for U.S. Appl. No. 12/770,153, filed Apr. 29, 2010; 29 pages.
Notice of Allowance mailed Oct. 3, 2011 for U.S. Appl. No. 12/770,153, filed Apr. 29, 2010; 12 pages.

* cited by examiner

OV=0          OV=2P

METHOD AND APPARATUS FOR ANGULAR-RESOLVED SPECTROSCOPIC LITHOGRAPHY CHARACTERIZATION

CROSS-REFERENCE TO RELATED APPLICATIONS

This application is related to U.S. application Ser. Nos. 13/249,566, 12/805,852, 11/203,418 and 10/918,742, which are all incorporated by reference herein in their entireties.

BACKGROUND OF THE INVENTION

1. Field of the Invention

The present invention relates to methods of inspection usable, for example, in the manufacture of devices by lithographic techniques and to methods of manufacturing devices using lithographic techniques.

2. Background Art

In a manufacturing process using a lithographic projection apparatus, a pattern (e.g. in a mask) is imaged onto a substrate that is at least partially covered by a layer of radiation-sensitive material (resist) by the changes of either optical properties or surface physical properties of the resist. Alternatively, the imaging step may use a resistless process such as etched grating or nano-imprint technology. Prior to this imaging step, the substrate may undergo various procedures, such as priming, resist coating and a soft bake. After exposure, the substrate may be subjected to other procedures, such as a post-exposure bake (PEB), development, a hard bake and measurement/inspection of the imaged features. This array of procedures is used as a basis to pattern an individual layer of a device, e.g. an IC. Such a patterned layer may then undergo various processes such as etching, ion-implantation (doping), metallization, oxidation, chemical-mechanical polishing, etc., all intended to finish off an individual layer. If several layers are required, then the whole procedure, or a variant thereof, will have to be repeated for each new layer. Eventually, an array of devices will be present on the substrate (wafer). These devices are then separated from one another by a technique such as dicing or sawing, whence the individual devices can be mounted on a carrier, connected to pins, etc.

The measurement and inspection step after development of the resist (or substrate surface in the case of etching), referred to as in-line because it is carried out in the normal course of processing production substrates, typically serves two purposes. Firstly, it is desirable to detect any target areas where the pattern in the developed resist is faulty. If a sufficient number of target areas are faulty, the substrate can be stripped of the patterned resist and re-exposed, hopefully correctly, rather than making the fault permanent by carrying out a process step, e.g., an etch, with a faulty pattern. Secondly, the measurements may allow errors in the lithographic apparatus, e.g. illumination settings or exposure dose, to be detected and corrected for in subsequent exposures. However, many errors in the lithographic apparatus cannot easily be detected or quantified from the patterns printed in resist. Detection of a fault does not always lead directly to its cause. Thus, a variety of off-line procedures for detecting and measuring errors in the lithographic apparatus are known. These may involve replacing the substrate with a measuring device or carrying out exposures of special test patterns, e.g., at a variety of different machine settings. Such off-line techniques take time, often a considerable amount, during which the end products of the apparatus will be of an unknown quality until the measurement results are made available. Therefore, in-line techniques, ones which can be carried out at the same time as production exposures, for detecting and measuring errors in the lithographic apparatus, are usually preferred.

Scatterometry is one example of an optical metrology technique that can be used for in-line measurements of CD and overlay. There are two main scatterometry techniques:

(1) Spectroscopic scatterometry measures the properties of scattered light at a fixed angle as a function of wavelength, usually using a broadband light source such as xenon, deuterium, or halogen based light source such as a xenon arc lamp. The fixed angle can be normally incident or obliquely incident.

(2) Angle-resolved scatterometry measures the properties of scattered light at a fixed wavelength as a function of angle of incidence, usually using a laser as a single wavelength light source.

The structure giving rise to a reflected spectrum is reconstructed, e.g., using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though light scattering can also be calculated by other techniques such as Finite Difference Time Domain (FDTD) or Integral Equation techniques.

A problem with known angle-resolved scatterometry techniques is that they only detect one wavelength at a time so spectra with more than one wavelength have to have those wavelengths time-multiplexed, which increases the total acquisition time taken to detect and process the spectra. In spectroscopic scatterometry, an extended light source with a large etendue is used. Since a small grating must be illuminated with a small spread in angle of incidence, a lot of light from this extended source is wasted. This results in low light levels on the detector that lead to long acquisition times, which have a negative impact on throughput. If short acquisition times are chosen, the measurement results might not be stable.

BRIEF SUMMARY OF THE INVENTION

Accordingly, it would be advantageous, for example, to provide a method of measuring overlay and grating shape parameters (such as grating asymmetry and alignment) during manufacture of devices using lithographic techniques and measurement of an angle-resolved spectrum in a pupil plane (or back focal plane) of a high NA (numerical aperture) lens. Projection system aberrations, etc. can also be measured in order to be corrected or compensated for.

Embodiments of the present invention may encompass hardware that is capable of measuring angle-resolved spectra at multiple wavelengths simultaneously, of carrying out immersion scatterometry and a focus measurement method for an angle-resolved scatterometer, and of measuring intensity noise of a radiation source with a 2-D detector array. Furthermore, embodiments of the present invention may encompass applications of the hardware including measuring overlay through the measurement of asymmetry of scattered light and measuring small line shape variations via Rayleigh anomalies and high diffraction orders of scattered light.

Although specific reference may be made in this text to the use of the apparatus according to the invention in the manufacture of ICs, it should be explicitly understood that such an apparatus has many other possible applications. For example, it may be employed in the manufacture of integrated optical systems, guidance and detection patterns for magnetic domain memories, liquid-crystal display panels, thin-film magnetic heads, etc. The skilled artisan will appreciate that, in the context of such alternative applications, any use of the terms "reticle", "wafer" or "die" in this text should be considered as being replaced by the more general terms "mask", "substrate" and "target portion", respectively.

In the present document, the terms "radiation" and "beam" are used to encompass all types of electromagnetic radiation, including ultraviolet radiation (e.g. with a wavelength of 365, 248, 193, 157 or 126 nm) and EUV (extreme ultra-violet radiation, e.g., having a wavelength in the range 5-20 nm), as well as particle beams, such as ion beams or electron beams.

BRIEF DESCRIPTION OF THE DRAWINGS/FIGURES

Embodiments of the invention will now be described, by way of example only, with reference to the accompanying schematic drawings in which corresponding reference symbols indicate corresponding parts and in which.

Figure 15A:
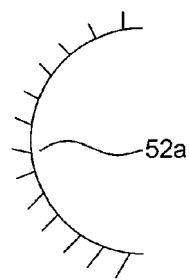
Figure 15B:
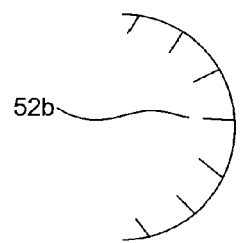
Figure 15C:
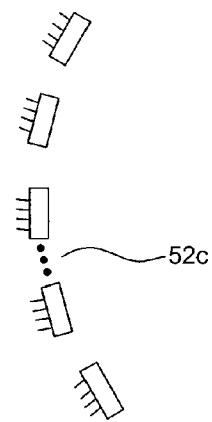

FIGS. 15A-C show a concave mirror, a convex mirror, and a plurality of plane mirrors tilted at different angles, according to various embodiments of the present invention.

DETAILED DESCRIPTION OF THE INVENTION

Figure 1:
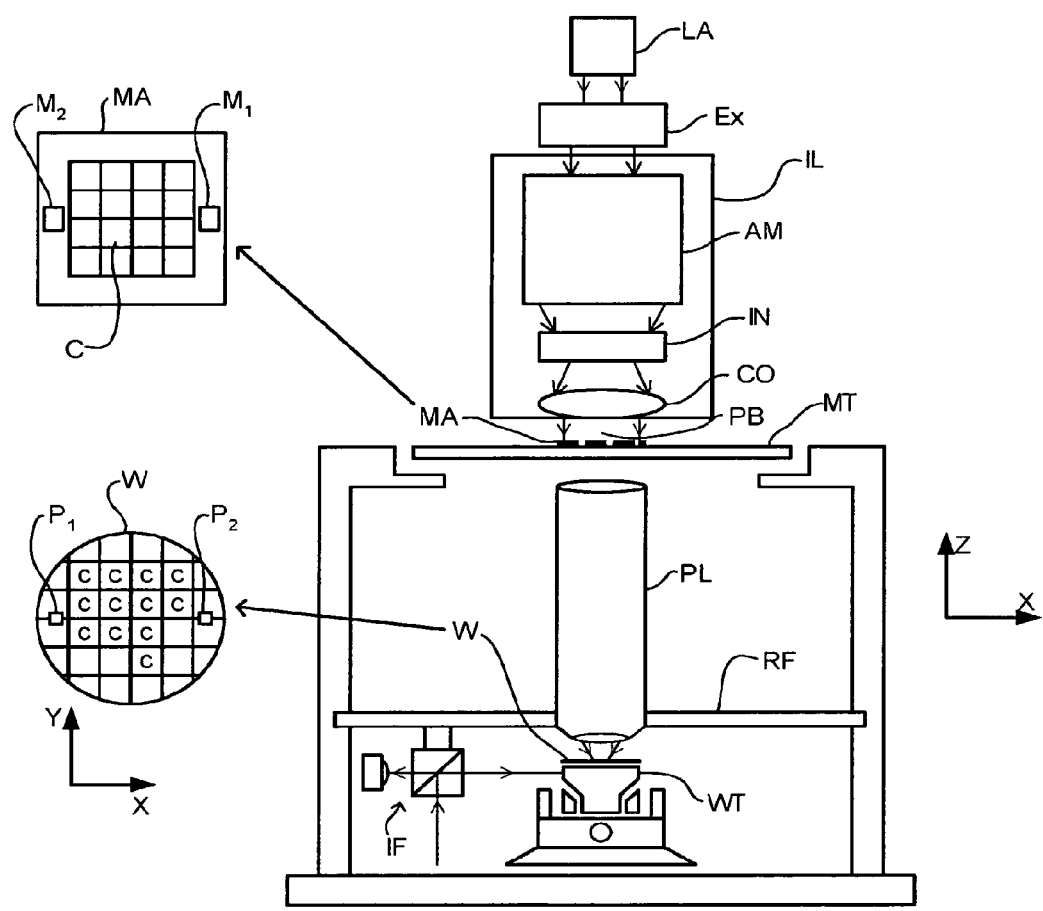
FIG. 1 depicts a lithographic projection apparatus that may be used to perform a method according to an embodiment of the invention.

FIG. 1 schematically depicts a lithographic projection apparatus useable in a method according to an embodiment of the invention. The apparatus comprises:

a radiation system Ex, IL, for supplying a projection beam PB of radiation (e.g. DUV radiation), which in this particular case also comprises a radiation source LA;

a first object table (mask table) MT provided with a mask holder for holding a mask MA (e.g. a reticle), and connected to a first positioning device for accurately positioning the mask with respect to item PL;

a second object table (substrate table) WT provided with a substrate holder for holding a substrate W (e.g. a resist-coated silicon wafer), and connected to a second positioning device for accurately positioning the substrate with respect to item PL;

a projection system ("projection lens") PL (e.g. a refractive lens system) for imaging an irradiated portion of the mask MA onto a target portion C (e.g. comprising one or more dies) of the substrate W.

As here depicted, the apparatus is of a transmissive type (e.g. has a transmissive mask). However, in general, it may also be of a reflective type, for example (e.g. with a reflective mask). Alternatively, the apparatus may employ another kind of patterning device, such as a programmable mirror array of a type as referred to above.

The source LA (e.g. an excimer laser) produces a beam of radiation. This beam is fed into an illumination system (illuminator) IL, either directly or after having traversed conditioning means, such as a beam expander Lx, for example. The illuminator IL may comprise adjusting means AM for setting the outer and/or inner radial extent (commonly referred to as σ-outer and σ-inner, respectively) of the intensity distribution in the beam. In addition, it will generally comprise various other components, such as an integrator IN and a condenser CO. In this way, the beam PB impinging on the mask MA has a desired uniformity and intensity distribution in its cross-section.

It should be noted with regard to FIG. 1 that the source LA may be within the housing of the lithographic projection apparatus (as is often the case when the source LA is a mercury lamp, for example), but that it may also be remote from the lithographic projection apparatus, the radiation beam which it produces being led into the apparatus (e.g. with the aid of suitable directing mirrors); this latter scenario is often the case when the source LA is an excimer laser. The current invention and claims encompass both of these scenarios.

The beam PB subsequently intercepts the mask MA, which is held on a mask table MT. Having traversed the mask MA, the beam PB passes through the projection lens PL, which focuses the beam PB onto a target portion C of the substrate W. With the aid of the second positioning device (and an interferometric measuring device IF), the substrate table WT can be moved accurately, e.g. so as to position different target portions C in the path of the beam PB. Similarly, the first positioning device can be used to position the mask MA accurately with respect to the path of the beam PB, e.g. after mechanical retrieval of the mask MA from a mask library, or during a scan. In general, movement of the object tables MT, WT will be realized with the aid of a long-stroke module (coarse positioning) and a short-stroke module (fine positioning), which are not explicitly depicted in FIG. 1. However, in the case of a stepper (as opposed to a step-and-scan apparatus) the mask table MT may just be connected to a short stroke actuator, or may be fixed.

The depicted apparatus can be used in two different modes:

1. In step mode, the mask table MT is kept essentially stationary, and an entire mask image is projected at one time (i.e. a single "flash") onto a target portion C. The substrate table WT is then shifted in the X and/or Y directions so that a different target portion C can be irradiated by the beam PB;

2. In scan mode, essentially the same scenario applies, except that a given target portion C is not exposed in a single "flash". Instead, the mask table MT is movable in a given direction (the so-called "scan direction", e.g. the Y direction) with a speed v, so that the projection beam PB is caused to scan over a mask image, concurrently, the substrate table WT is simultaneously moved in the same or opposite direction at a speed V=Mv, in which M is the magnification of the projection system PL (typically, M=¼ or ⅕). In this manner, a relatively large target portion C can be exposed, without having to compromise on resolution.

Figure 2:
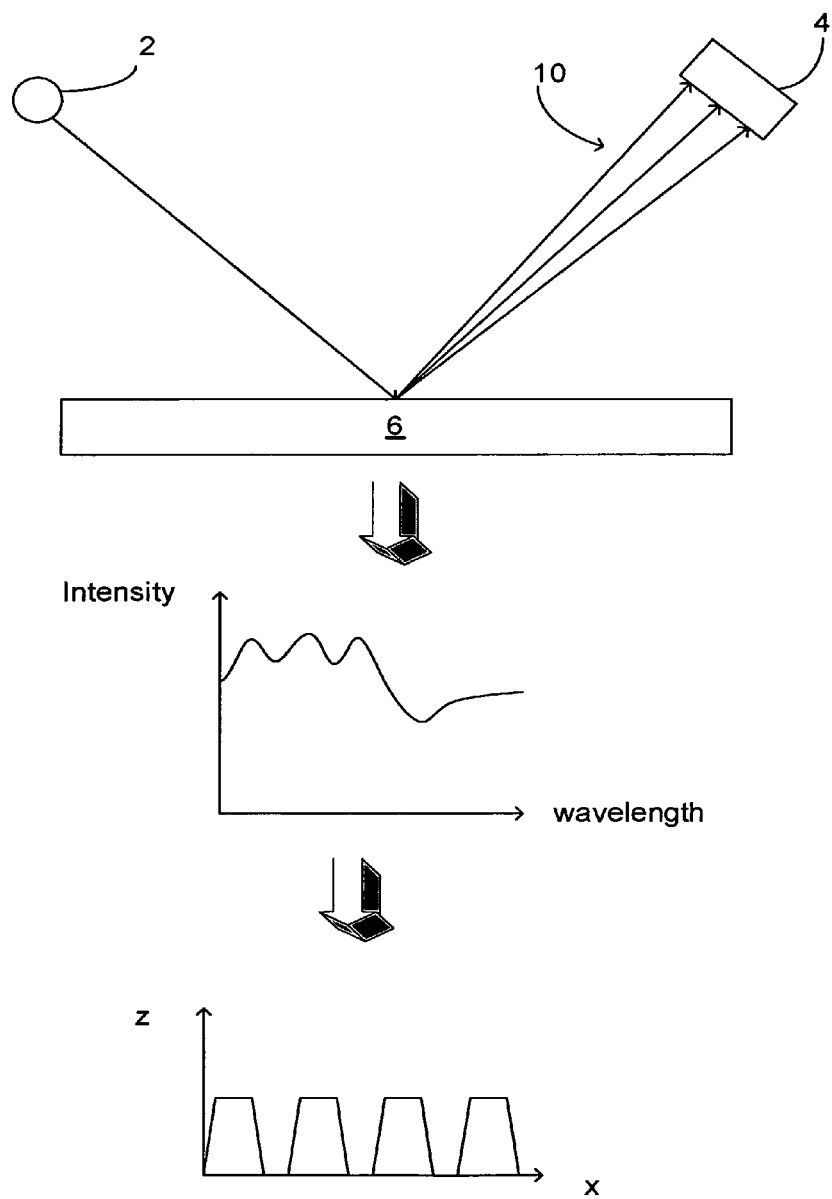
FIG. 2 depicts a scatterometer.

One or more properties of the surface of a substrate 6 may be determined using a scatterometer such as that depicted in FIG. 2. In an embodiment, the scatterometer comprises a broadband (white light) radiation source 2, which directs radiation onto a substrate 6. An extended broadband radiation source may be configured to provide the radiation beam with a wavelength of at least 50 nm to the substrate surface. The reflected radiation is passed to a spectrometer detector 4, which measures a spectrum 10 (intensity as a function of wavelength) of the specular reflected radiation. From this data, the structure or profile giving rise to the detected spectrum may be reconstructed, e.g. by Rigorous Coupled Wave Analysis and non-linear regression or by comparison with a library of simulated spectra as shown at the bottom of FIG. 2. In general, for the reconstruction, the general form of the structure is known and some parameters are assumed from knowledge of the process by which the structure was made, leaving only a few parameters of the structure to be determined from the scatterometry data.

The scatterometer may be a normal-incidence scatterometer or an oblique-incidence scatterometer. Variants of scatterometry may also be used in which the reflection is measured at a range of angles of a single wavelength, rather than the reflection at a single angle of a range of wavelengths.

Figure 3:
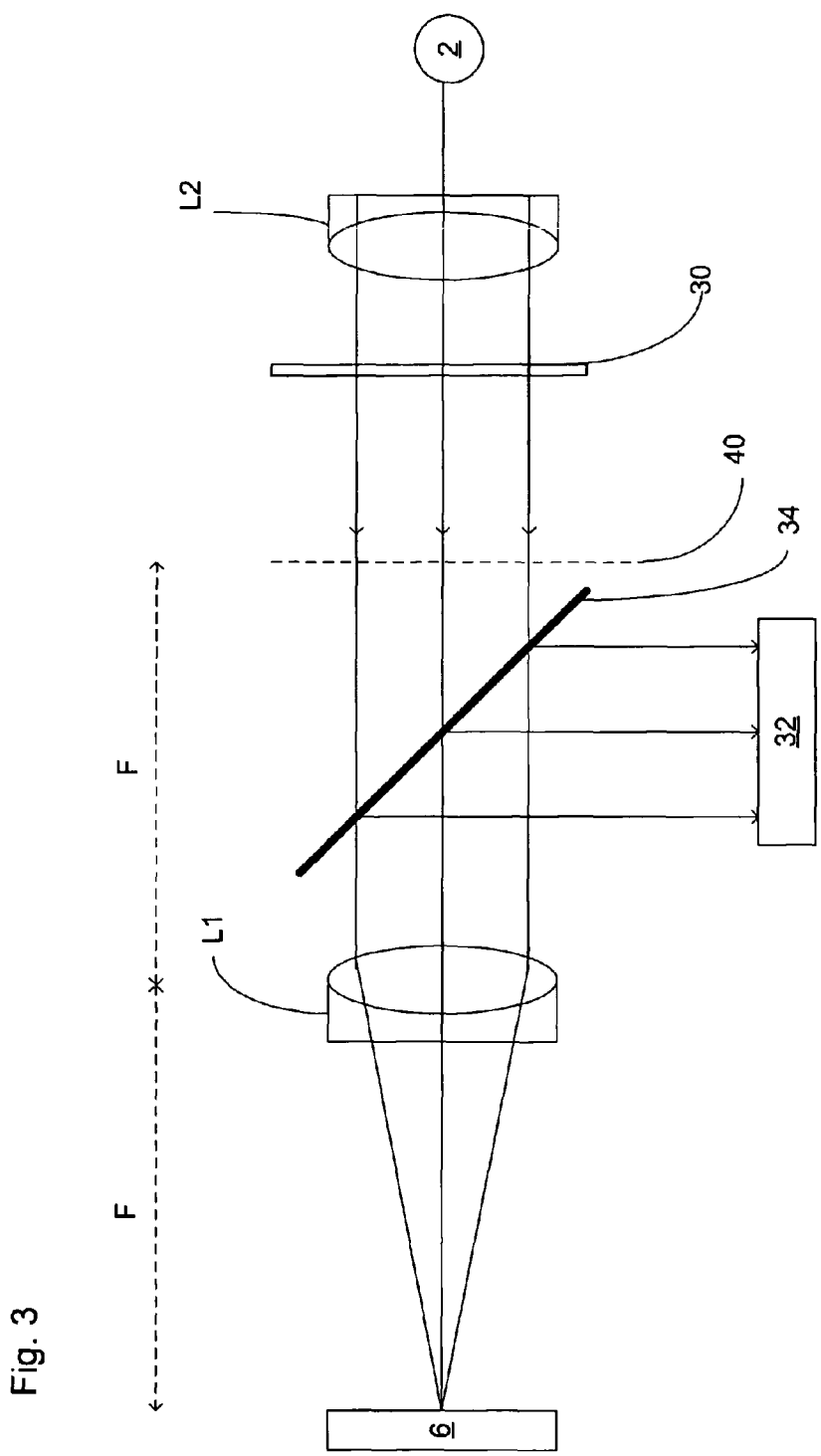
FIG. 3 depicts the general operating principle of measuring an angle-resolved spectrum in the pupil plane of a high NA lens according to an embodiment of the invention.

In one or more embodiments described below, there is used a scatterometer configured to measuring a property of a substrate by measuring, in a pupil plane 40 of a high NA lens, a property of an angle-resolved spectrum reflected from the substrate surface 6 at a plurality of angles and wavelengths as shown in FIG. 3. The scatterometer comprises a radiation source 2 configured to project radiation onto the substrate and a detector 32 configured to detect the reflected spectra. The pupil plane is the plane in which the radial position of radiation defines the angle of incidence and the angular position defines the azimuth angle of the radiation and any substantially conjugate plane. The detector 32 is placed in the pupil plane of the high NA lens. The NA is high and, in an embodiment, at least 0.9 or at least 0.95. Immersion scatterometers may even have lenses with a NA over 1.

Previous angle-resolved scatterometers have only measured the intensity of scattered radiation. An embodiment of the present invention allows several wavelengths to be measured simultaneously at a range of angles. The properties measured by the scatterometer for different wavelengths and angles may include the intensity of transverse magnetic (TM) and transverse electric (TE) polarized radiation and the phase difference between the TM and TE polarized radiation.

Using a broadband light source (i.e. one with a wide range of light frequencies or wavelengths—and therefore of colors) is possible, which gives a large etendue, allowing the mixing of multiple wavelengths. The plurality of wavelengths in the broadband light, in an embodiment, each has a bandwidth of, say, δλ and a spacing, therefore, of at least 2 δλ (i.e. twice the wavelength). Several "sources" of radiation can be different portions of an extended radiation source that have been split using, say, fiber bundles. In this way, angle-resolved scatter spectra can be measured at multiple wavelengths in parallel. A 3-D spectrum (wavelength and two different angles) may be measured, which contains more information than a 2-D spectrum. This allows more information to be measured which increases metrology process robustness.

A scatterometer of an embodiment of the present invention is shown in FIG. 3. The light source 2 is focused using lens system L2 through interference filter 30 and is focused onto substrate 6 via a microscope objective lens L1. The radiation is then reflected via partially reflective surface 34 into a CCD detector in the back projected pupil plane 40 in order to have the scatter spectrum detected. The pupil plane 40 is at the focal length of the lens system L1. A detector and high NA lens are placed at the pupil plane. The pupil plane may be re-imaged with auxiliary optics since the pupil plane of a high NA lens is usually located inside the lens.

The pupil plane of the reflector light is imaged on the CCD detector with an integration time of, for example, 40 milliseconds per frame. In this way, a two-dimensional angular scatter spectrum of the substrate target is imaged on the detector. The detector may be, for example, an array of CCD detectors or CMOS detectors. The processing of the spectrum gives a symmetrical detection configuration and so sensors can be made rotationally symmetrical. This allows the use of a compact substrate table because a target on the substrate can be measured at any rotational orientation relative to the sensor. All the targets on the substrate can be measured by a combination of a translation and a rotation of the substrate.

A set of interference filters 30 may be available to select a wavelength of interest in the range of, say, 405-790 nm or even lower, such as 200-300 nm. The interference filter may be tunable rather than comprising a set of different filters. A grating could be used instead of one or more interference filters.

The substrate 6 (or even the reflective surface 34) may be a grating. The grating may be printed such that after development, a series of bars are formed of solid resist lines. The bars may alternatively be etched into the substrate. This pattern is sensitive to comatic aberrations in a lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. One or more parameters of the grating, such as line widths and shapes, may be input to the reconstruction process from knowledge of the printing step and/or other scatterometry processes.

In transmission metallic gratings with rectangular slits, complex photonic band structures (CPBS) are shown to exhibit strong discontinuities, which are located on Wood-Rayleigh anomalies and reveal two types of resonance, which are referred to as horizontal and vertical surface-plasmon resonances. Spectral position and width of peaks in the spectrum can be directly extracted from CPBS for both horizontal and vertical resonances. In this way, the radiation coming off a transmission metallic grating can have its spectrum analyzed and one or more properties of the grating determined by the strong discontinuities located on the Wood-Rayleigh anomalies. Wood-Rayleigh anomalies occur upon the variation of wavelength or angle of incidence, giving an additional propagating diffraction order. The greater the beam width, the greater the lateral displacement of the beam.

An embodiment of the present invention detects the spectrum and creates a symmetrical pupil plane image from which the discontinuities can be measured and one or more grating properties therefore calculated.

According to an embodiment of the invention, the scatterometer may be adapted to measure the overlay of two misaligned periodic structures by measuring asymmetry in the reflected spectrum, the asymmetry being related to the extent of the overlay.

In an embodiment, the scatterometer is adapted to measure the overlay of two misaligned gratings or periodic structures by measuring asymmetry in the reflected spectrum and/or the detection configuration, the asymmetry being related to the extent of the overlay. Thanks to the symmetrical detection configuration, any asymmetry is clearly distinguishable. This provides a straightforward way to measure misalignment in the gratings.

One type of substrate pattern used is shown in FIG. 4. A grating 14 has a second grating 12 printed on top of it. The amount by which the grating 12 is offset with respect to grating 14 is known as the overlay 22.

Figure 4A:
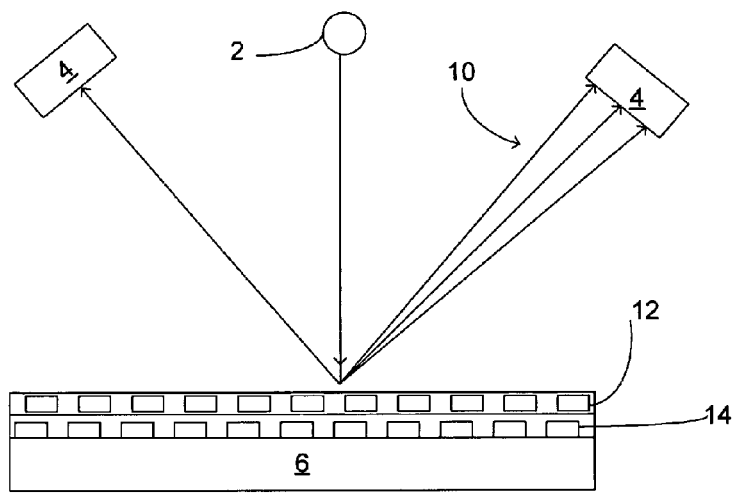
FIGS. 4a and 4b depict the use of an embodiment of the present invention in determining overlay.

Note that in the embodiment shown in FIG. 4a, the radiation source 2 illuminates the object symmetrically with respect to the surface normal and the scatterometry detector measures scatter radiation from several angles, although a source which illuminates the object from an oblique angle is also possible.

Overlay metrology is based on the measurement of an asymmetry in the angular scatter spectrum. Symmetric structures yield symmetric angular spectra and an asymmetry in the target shows up as an asymmetry in the angular scatter spectrum. This property is the basis of overlay metrology using angle-resolved scatterometry.

Two overlapping but misaligned gratings 12 and 14 made of bars with width 20 form one composite asymmetric target. The resulting asymmetry in the angular scatter spectrum is detected with the angle-resolved scatterometer 4 shown in FIG. 3 and used to derive the overlay 22 in the following manner:

Two grating pairs are used with a deliberate bias of +d and −d in, respectively, the first and second pair. In other words, grating 12 is shifted in one direction in one pair (as shown in FIG. 4) and in the opposite direction in the other pair (not shown). The actual transverse shift between the gratings in each pair is therefore $X_1=OV+d$ and $X_2=OV-d$, OV being the overlay 22.

When the grating pairs are aligned, the overlay is 0 and if the intensity of the illumination incident on the gratings is $I_{ill}$ and the intensity of the radiation reflected off the gratings is $I_{+1}$ in a first direction and $I_{-1}$ in the opposite direction but in the same plane, when the overlay, OV=0, $$I_{+1}=I_{-1}. \quad (1)$$

However, if $$OV \neq 0,$$

$$I_{+1} \neq I_{-1}. \quad (2)$$

For a small overlay, the intensity difference is proportional to the overlay:

$$I_{+1}-I_{-1}=K \times OV. \quad (3)$$

K is a constant and is process dependent and therefore unknown.

Figure 4B:
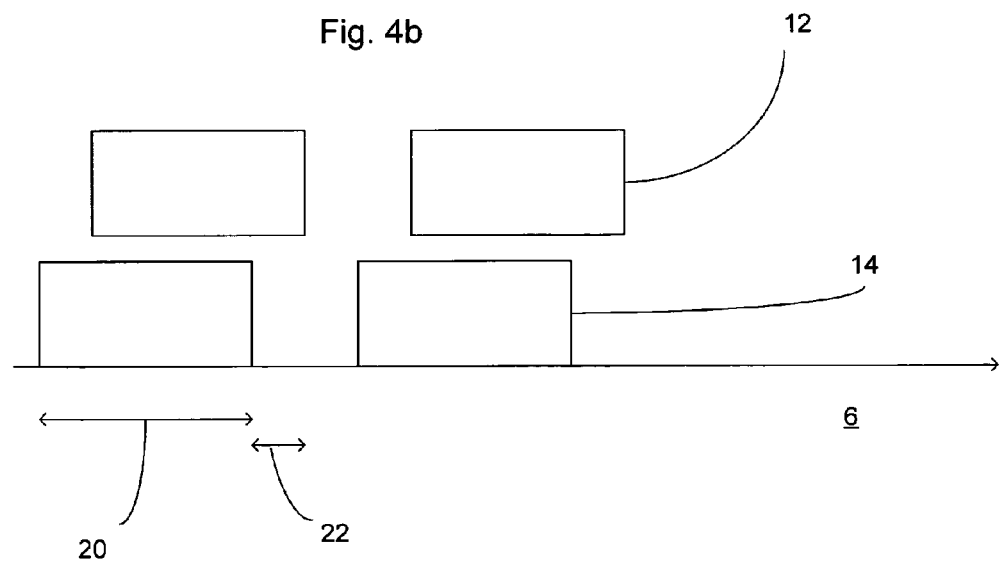

In order to calibrate the overlay metrology with the scatterometer according to an embodiment of the present invention, two grating targets are used; one with the overlay shown in FIG. 4b and a second with the exact reverse overlay, so the upper grating 12 is displaced to the left rather than the right with respect to the bottom grating 14. The overlay in the first set-up is OV+d (distance 22 in FIG. 4b) and the overlay in the second set-up is OV−d.

So, for $$OV+d,$$

asymmetry $$A_+=K(OV+d) \quad (4)$$

and for $$OV-d,$$

asymmetry $$A_-=K(OV-d). \quad (5)$$

The scaling factor K can be eliminated:

$$OV = d\frac{A_+ + A_-}{A_+ - A_-} \quad (6)$$

The overlay can therefore be calculated using measurements of the asymmetry in the angle-resolved scatter spectrum.

An advantage of this method compared to previously known methods is the fact that only two gratings are required. Moreover, in principle, the method can also work for 2-D gratings: in that case only 2 gratings are required for a complete (x,y) overlay measurement. This is a significant improvement compared to, say, 6 gratings that spectroscopic scatterometry methods use.

The analysis of xy overlay metrology using 2-D gratings is as follows:

Two gratings have an amplitude transmission of f(x, y) and g(x, y). These gratings are periodic in two directions and their transmissions can therefore be written as a Fourier series:

$$f(x, y) = \sum_n \sum_m F_{n,m} e^{-j(nx+my)} \quad (7)$$

$$g(x, y) = \sum_p \sum_q G_{p,q} e^{-j(px+qy)}$$

Both gratings have an equal period and for simplicity the periods of the gratings have been normalized to $2\pi$ for the following calculations. The coefficients $F_{n,m}$ and $G_{p,q}$ can be interpreted as diffraction efficiencies that depend on the grating shape, wavelength and polarization. The two gratings overlap with a relative overlay of $x_0$ and $y_0$ in, respectively, the x and y directions. The total transmission t can be written as:

$$t(x, y) = f(x, y)g(x - x_0, y - y_0) \quad (8)$$

$$= \sum_n \sum_m \sum_p \sum_q F_{n,m} G'_{p,q} e^{-j((p+n)x+(q+m)y)}$$

where:

$$G'_{p,q}=G_{p,q}e^{j(px_0+qy_0)} \quad (9)$$

The variables can be adjusted as follows:

$$p+n=a \Rightarrow p=a-n$$

$$q+m=b \Rightarrow q=b-m$$

Substituting these expressions in the Fourier series of t(x,y) yields:

$$t(x, y) = \sum_n \sum_m \sum_p \sum_q F_{n,m} G'_{n,m} e^{-j((p+n)x+(q+m)y)} \quad (10)$$

-continued
$$= \sum_a \sum_b T_{a,b} e^{-j(ax+by)}$$

where:

$$T_{a,b} = \sum_n \sum_m F_{n,m} G'_{a-n,b-m} \quad (11)$$

$T_{a,b}$ can be interpreted as the amplitude of the diffraction order (a,b). It can be see that this amplitude generally depends on the overlay in the x and y direction.

For simplicity, only diffraction orders running in the x-direction are considered. The analysis that follows can also be done for diffraction orders in the y-direction. This would only require an adjustment of variables.

For diffraction orders that run in the x-direction, b=0, so for the amplitude of two diffraction orders a and −a:

$$T_{a,0} = \sum_n \sum_m F_{n,m} G_{a-n,-m} e^{j((a-n)x_0 - my_0)} \quad (12)$$

$$T_{-a,0} = \sum_n \sum_m F_{n,m} G_{-a-n,-m} e^{j((-a-n)x_0 - my_0)}$$

taking the factor $e^{\pm jax_0}$ in front of the summation yields:

$$T_{a,0} = e^{jax_0} \sum_n \sum_m F_{n,m} G_{a-n,-m} e^{-j(nx_0 + my_0)} \quad (13)$$

$$T_{-a,0} = e^{-jax_0} \sum_n \sum_m F_{n,m} G_{-a-n,-m} e^{-j(nx_0 + my_0)}$$

$$= e^{-jax_0} \sum_{-n} \sum_m F_{-n,m} G_{-a+n,-m} e^{j(nx_0 - my_0)}$$

Assuming that both gratings are symmetric in the x-direction:

$$F_{-n,m} = F_{n,m}$$

$$G_{-n,m} = G_{n,m} \quad (14)$$

Using this property yields for the diffracted amplitudes:

$$T_{a,0} = e^{jax_0} \sum_n \sum_m F_{n,m} G_{a-n,-m} e^{j(nx_0 + my_0)} \quad (15)$$

$$T_{-a,0} = e^{-jax_0} \sum_n \sum_m F_{n,m} G_{-a-n,-m} e^{-j(nx_0 - my_0)}$$

The scatterometer measures the intensities of the diffracted fields, giving:

$$I_{\pm a,0} = |T_{\pm a,0}|^2 \quad (16)$$

Evaluation of this expression shows that the intensity can be written in the form:

$$I_{a,0} = \sum_n \sum_m B_{n,m} \cos(\varepsilon_{n,m} - nx_0 - my_0) \quad (17)$$

$$I_{-a,0} = \sum_n \sum_m B_{n,m} \cos(\varepsilon_{n,m} + nx_0 - my_0)$$

where the amplitudes $B_{n,m}$ and phases $\epsilon_{n,m}$ depend on the grating shapes, illumination wavelength and illumination polarization. Taking the difference of the +1 and −1 order yields an asymmetry $A_x$ that runs in the x-direction:

$$A_x = I_{1,0} - I_{-1,0} \quad (18)$$

$$= \sum_n \sum_m B_{n,m} \cos(\varepsilon_{n,m} - nx_0 - my_0) -$$

$$\sum_n \sum_m B_{n,m} \cos(\varepsilon_{n,m} + nx_0 - my_0)$$

$$= \sum_n \sum_m 2B_{n,m} \sin(\varepsilon_{n,m} - my_0) \sin(nx_0)$$

In practice the overlay is small compared to the pitch of the gratings. For example, the pitch is often of the order of 1 μm and the maximum overlay is of the order of 60 nm. The expression above can therefore be linearized and only the linear terms in $x_0$ and $y_0$ retained:

$$A_x = \sum_n \sum_m 2B_{n,m} \sin(\varepsilon_{n,m} - my_0) \sin(nx_0) \quad (19)$$

$$= \sum_n \sum_m 2B_{n,m} [\sin(\varepsilon_{n,m}) \cos(my_0) -$$

$$\cos(\varepsilon_{n,m}) \sin(my_0)] \sin(nx_0)$$

$$\cong \sum_n \sum_m 2B_{n,m} [\sin(\varepsilon_{n,m}) - \cos(\varepsilon_{n,m}) my_0] nx_0$$

$$= x_0 K_0 + K_{xy} x_0 y_0$$

where $$K_0 = \sum_n \sum_m 2nB_{n,m} \sin(\varepsilon_{n,m}) \quad (20)$$

$$K_{xy} = \sum_n \sum_m 2mnB_{n,m} \cos(\varepsilon_{n,m})$$

It can be seen that there is a coupling term: The asymmetry in the x-direction is also a function of the y-overlay via the coupling term $K_{xy}$. If the 2-D grating has 90° rotation symmetry and if the light is polarized at 45°, then we can write for the asymmetry in the x and y directions:

$$A_x = x_0 K_0 + K_{xy} x_0 y_0$$

$$A_y = y_0 K_0 + K_{xy} x_0 y_0 \quad (21)$$

These equations are the basis for xv overlay metrology with two 2-D grating pairs. In the first grating pair, a bias of +d is introduced in the upper grating and in the second grating pair, a bias of −d is introduced. This bias is applied in both the x and y direction. Four asymmetry terms can now be measured: An x and y asymmetry in the first grating pair and an x and y asymmetry in the second grating pair are shown as:

$$A_{1x} = K_0(OV_x + d) + K_{xy}(OV_y + d)(OV_x + d)$$

$$A_{1y} = K_0(OV_y + d) + K_{xy}(OV_y + d)(OV_x + d)$$

$$A_{2x}=K_0(OV_x-d)+K_{xy}(OV_y-d)(OV_x+d)$$

$$A_{2y}=K_0(OV_y-d)+K_{xy}(OV_y-d)(OV_x-d) \quad (22)$$

This gives four non-linear equations with four unknowns $K_0$, $K_{xy}$, $OV_x$ and $OV_y$, which can be solved to give the overlay.

In an embodiment, one or more apertures may be provided to the scatterometer to mimic lithography exposure conditions when the grating pattern(s) was created. The apertures may then be used in the creation of the angle-resolved spectroscopic image of the grating pattern(s) using the scatterometer.

In an embodiment, it is possible to immerse at least part of the space between the substrate and the detector in liquid, more specifically, the space between lens L1 and the substrate 6 as shown in FIG. 3. The liquid may be water. This has an advantage of increasing the spatial bandwidth of the medium between the substrate 6 and the lens L1. This means that a diffraction that would be evanescent, for example, in air can propagate and be captured by the lens. With immersion of the space, therefore, it becomes possible to detect a higher diffraction order that contains more detailed information about the grating under investigation than with, for example, air in the space. In an embodiment, the numerical aperture (NA) of the scatterometer is at least 0.9, even 0.95 or above 1.

Immersing the space between L1 and the object with a high refractive index fluid increases the spatial bandwidth of the medium and allows the propagation of a higher diffraction order for smaller pitches. The smallest pitch that creates a propagating first order spectrum is $$\frac{\lambda}{(2NA)}.$$

Assuming NA equals 1.3 and λ equals 400 nm, this yields a minimum pitch of 154 nm. This corresponds to a critical dimension (CD) or reconstructed grating width of approximately 20 to 80 nm. When looking at a profile such as that shown in FIG. 2, the critical dimension is the mean width of a peak and the pitch is the distance from one peak to the next.

The immersion fluid should have a large index step with respect to, for example, the resist that is on the substrate 6. This may allow maximum contrast in the detector image. A possible liquid that fulfils such requirements is water.

Figure 5:
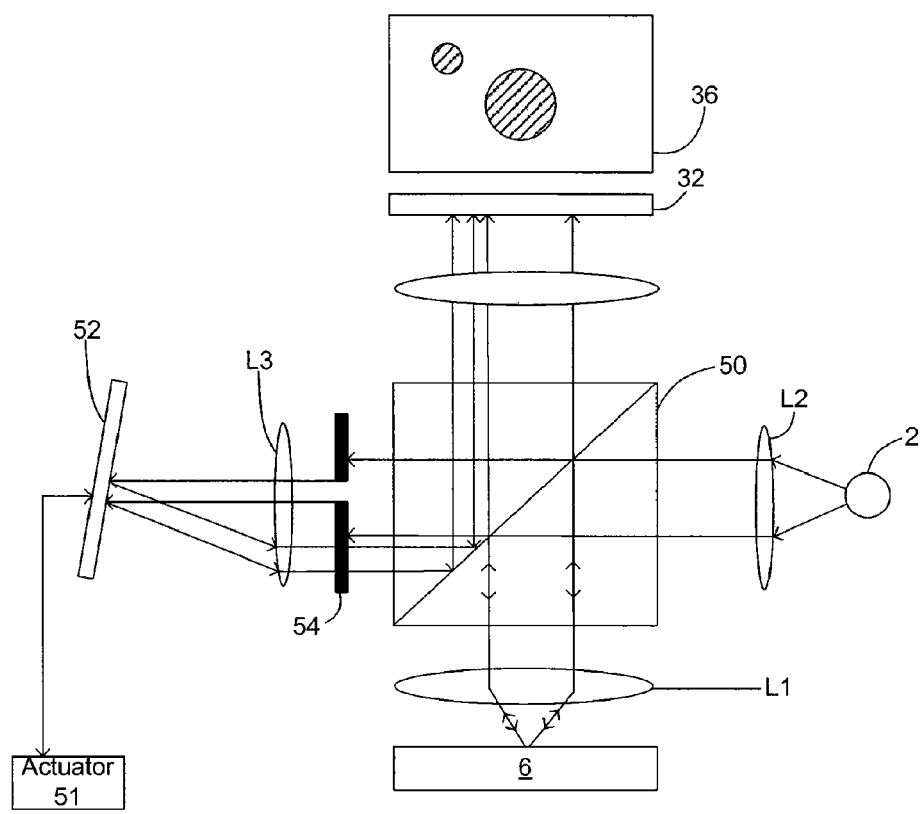
FIG. 5 depict the use of a non-polarizing beam splitter for coupling off a portion of a radiation beam according to an embodiment of the invention.

FIG. 5 shows, according to an embodiment of the invention, the use of one and the same detector to monitor the source output intensity and the intensity of scattered radiation, which avoids synchronization problems and allows a real-time compensation for source output variations.

The scatterometer may comprise a non-polarizing beam splitter and a tilted mirror for coupling off a portion of the radiation beam emitted from the radiation source for separate measurement with the same detector. In an embodiment, the portion of the radiation beam is used to measure the intensity of the radiation beam and the scatterometer may be adapted to compensate for fluctuations in intensity of the radiation beam. Advantages of using the same CCD detector for the intensity measurement beam alongside the main measurement beam are that no extra detector is required and so there is no difference in optical and thermal properties between a reference sensor and a metrology sensor; and there are no extra electronics required to trigger, read out and store the reference signal. Any intensity variations may be measured and compensated for.

A non-polarizing beam splitter 50 in the radiation path images scattered radiation on a two-dimensional detector 32.

An extra lens re-images the pupil plane onto the CCD detector. The intensity incident on the detector is shown as image 36. The non-polarizing beam splitter 50 also couples out a portion of the radiation beam to use it for monitoring intensity noise. Instead of measuring this radiation portion with a separate detector, the radiation is retro-reflected using tilted mirror 52 and transmitted to a separate part of the same detector 32. Tilted mirror 52 can be titled by an actuator 51. Further, although a plane tilted mirror 52 is shown, a concave mirror 52a, a convex mirror 52b, or a plurality of plane mirrors 52c tilted at different angles, can alternatively be used, as shown in FIGS. 15A-C, respectively. An optional pupil stop 54 limits the extent of the radiation portion and the mirror tilt ensures that the radiation portion is projected alongside the main radiation beam. The spectrum is imaged onto the detector 32 at the pupil plane of L1.

In previous methods, angle-resolved scatterometry has been done at a single wavelength. Measurements at different wavelengths would then have been done sequentially and the different wavelengths would be time multiplexed. However, time multiplexing of the wavelengths may degrade throughput.

In an embodiment, the scatterometer comprises a wavelength multiplexer between the radiation source and the substrate and a demultiplexer between the substrate and the detector. This allows several different wavelengths (or colors) to be measured simultaneously, giving more information in a shorter time frame and therefore robustness as discussed above.

In an embodiment, the surface area of the radiation source is split into N parts that are each coupled to a wavelength multiplexer, where N is the number of discrete wavelengths. This splitting can be done, for example, with fiber bundles and the like.

In an embodiment, the wavelength multiplexer comprises a dispersive element placed at a back-projected object plane. The dispersive element may be a grating or prism adapted to accommodate N discrete wavelengths each with a bandwidth δλ and a spacing of at least twice the bandwidth, i.e. 2 δλ. This may maximize the usage of an extended light source. Measurement of different wavelengths no longer has to be time-multiplexed because it can be done at the same time, and so a major advantage is that throughput is increased. The wavelength multiplexer may, alternatively or additionally, comprise a dispersive element placed at a pupil plane.

In an embodiment, the demultiplexer comprises a dispersive element placed at a pupil plane. One or more optical wedges may be inserted in the object plane to achieve well-defined separation of angle-resolved spectra in the pupil plane.

In an embodiment, an extended broadband radiation source such as a xenon, deuterium or quartz tungsten halogen light source is used. These sources have a large etendue that gives a surface area that can be split into discrete wavelengths and offer more information as discussed above. The wavelengths may be in the range of 193 to 800 nm.

In an embodiment, a dispersive prism or grating which combines N discrete wavelengths is used in the illumination branch (or the radiation path between the source 2 and the substrate 6 in FIG. 2) and a grating or prism is used in the detection branch (or the space between the radiation path between the substrate 6 and the detector 4) to spatially separate the wavelengths.

Figure 6:
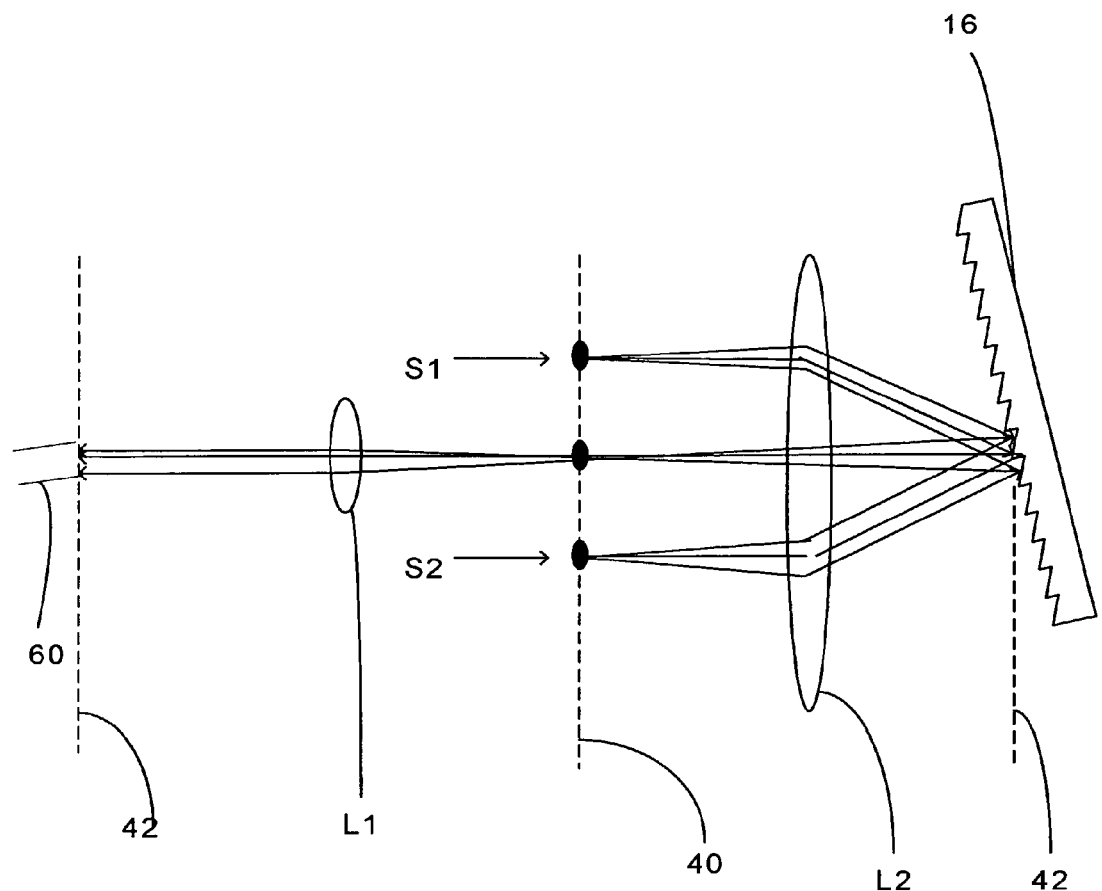
FIG. 6 depicts a wavelength multiplexer according to an embodiment of the invention.

An example of a multiplexing grating is shown in FIG. 6. Two light sources S1 and S2 are transmitted through a lens system L2 and strike a Littrow mounted grating 16 which is in the object plane 42 and are focused on the pupil plane 40 before being transmitted through a lens system L1 to another object plane 42 and optionally into an illumination fiber 60. The pupil plane contains rectangular apertures of suitable dimensions—the width determining the angular extent of the light incident on the grating. This angular extent and the grating pitch determine the bandwidth of the returning light that is transmitted via the aperture in the pupil plane. For example, a grating with 1200 lines per millimeter yields a dispersion of approximately 1.2 mrad/nm. An effective bandwidth of 4 nm corresponds to a full angular width of the illumination beam of 3.33 mrad. The spot size of the substrate 6 is approximately 40 μm and its NA is 0.95. The beam diameter on the grating is therefore approximately 23 mm. If the focal length of the lens L1 is 100 mm, then the width of the aperture holes in the pupil plane must be 333 μm. If an illumination fiber is used, then the illumination NA must be approximately 0.22.

Clearly more than two radiation sources (with different wavelengths) may be used at a time.

Figure 7:
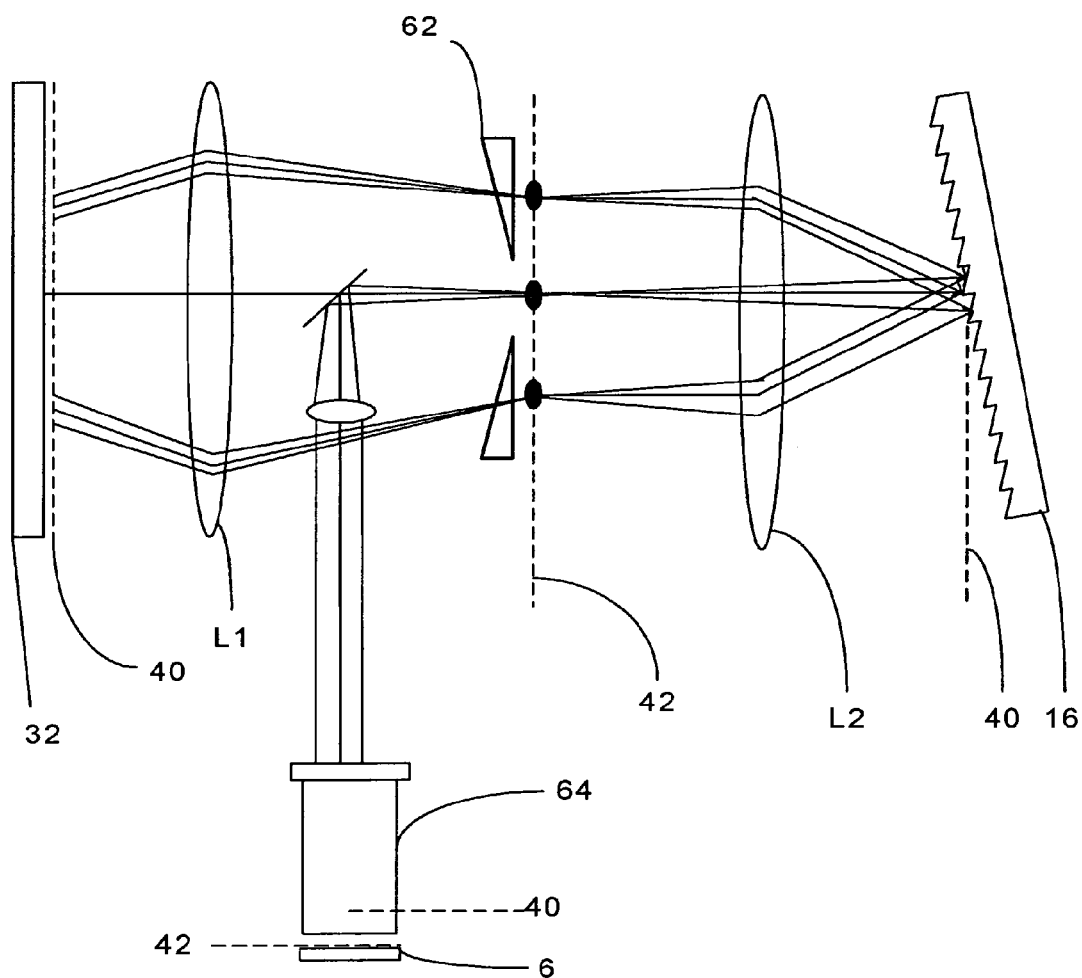
FIG. 7 depicts a wavelength demultiplexer according to an embodiment of the invention.

FIG. 7 shows an example of a wavelength demultiplexer in the detection branch. For simplicity, the separation of only two wavelengths is again shown. The demultiplexer is similar to the multiplexer, except that the grating is placed in the pupil plane and not in the object plane. The light that is diffracted by the grating in the Littrow mounted grating 16 is transmitted by the lens L2, which makes two object images with wavelengths δ1 and λ2 in the object plane. This plane may contain field stops with n holes (n=2 in this case), which should be sufficiently wide to avoid spatial filtering to avoid disturbing the spectrum. Each hole of the field stop 40 also has a wedge 62 with a unique wedge angle. This wedge 62 ensures that the angle-resolved scatter spectrum for each wavelength is imaged on a different part of the CCD detector 32. The CCD detector is based at the second pupil plane 40.

Since the wedges 62 can deflect the light in two directions, it is possible to realize an efficient filling of a CCD detector with many angle-resolved spectra.

Figure 8:
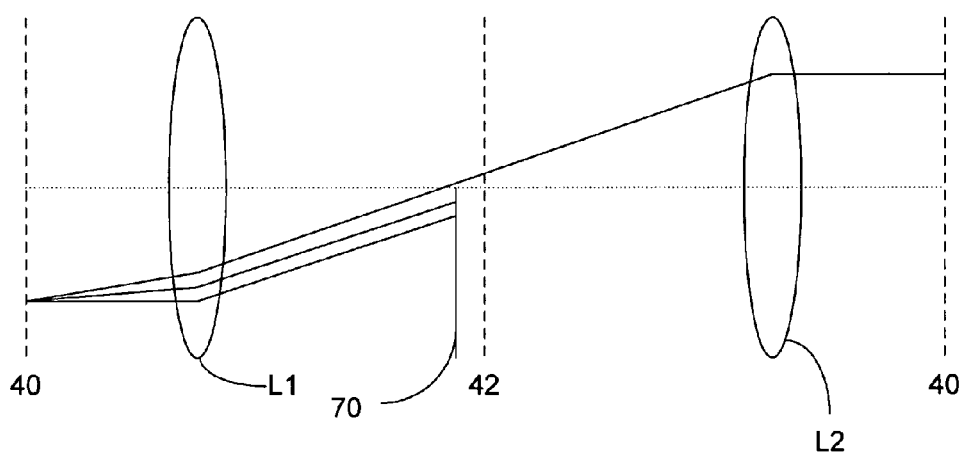
FIG. 8 depicts a knife edge at an intermediate object plane according to an embodiment of the invention.

In order to obtain reproducible results, the targets should be well focused. In order to achieve this, the pupil plane 40 of a high NA objective is imaged on a detector with a double telecentric system as shown in FIG. 8 according to an embodiment of the invention. In all embodiments, the NA is high, desirably at least 0.9.

A knife edge 70 in the intermediate object plane 42 blocks one half of the intermediate object image. The edge may be a Foucault knife-edge.

The knife-edge helps to focus the image of the radiation onto the substrate. For each orientation, the intensity in the outer regions (or practically speaking, in two halves) of the pupil plane 40 is sampled. In the case of a defocus, a difference in intensities $I1$ and $I2$ is produced. Focus F is given as:

$$F = k\frac{I1 - I2}{I1 + I2} \quad (23)$$

The proportionality factor k is independent of the image and needs to be determined only once, though since the focus sensor can be used in an integrating feedback loop, the precise value of k is not important.

Illumination sources are not always homogeneous and must be calibrated and corrected for in order to guarantee precise exposure of a substrate. Inhomogeneity may be caused by the illumination sources themselves, or by the roughness of a surface coating of one or more reflectors in the illumination path. Normalization of the illumination beam may be done using an aluminum mirror. However, this normalization may fail when the object to be measured (i.e., a grating or the substrate) generates higher diffraction orders. These cause tool induced shift errors in overlay applications.

In an embodiment, therefore, the scatterometry system further comprises one or more mirrors in the illumination beam. More specifically, the one or more mirrors may be a fiducial on the substrate table and may be made of aluminum. The one or more mirrors either tilt or exist at different tilt angles in order to create at least two images reflected at different angles. For each tilt angle, the detected spectrum shifts in the same direction as the direction of the tilt. These images are detected and combined into a differential equation, from which the illumination profile of the radiation beam may be determined. The resultant illumination profile is used to correct measurements of the property of the reflected spectrum at higher diffraction orders.

The measured signal, $M_0(k)$, is represented as:

$$M_0(k) = [A(-k)R_0(k) + A(-k \pm k_G)R_{\mp N}(x) + \ldots + A(-k \pm Nk_G)R_{\mp N}(x)]B(k) \quad (24)$$

where:
A(k) is the unknown illumination intensity at position k in the pupil plane;
B(k) is the unknown optical loss in the detection branch of the sensor; and
$R_{\pm N}$ is the diffraction efficiency of the $N^{th}$ order of the grating object.

In practice, the illumination intensity varies because of a slowly varying inhomogeneous illumination beam and surface roughness of the optics and coatings in the illumination path. The surface roughness of an optical coating generally gives rise to a grainy appearance of the illumination beam in the pupil plane.

A reference measurement may be carried out on a highly reflecting aluminum mirror, which yields the following measured signal:

$$M_M(k) = A(-k)R_M(k)B(k) \quad (25)$$

Normalizing the measurement of the object with the reference yields:

$$\frac{M_0(k)}{M_M(k)} = \frac{R_0(k)}{R_M(k)} + \frac{A(-k \pm k_G)}{A(-k)}\frac{R_{\mp 1}(x)}{R_M(k)} + \ldots + \frac{A(-k \pm Nk_G)}{A(-k)}\frac{R_{\mp N}(x)}{R_M(k)} \quad (26)$$

It can be seen that the losses in the detection branch are eliminated by this normalization.

However, inhomogeneities in the illumination are only eliminated for the zero diffraction order (i.e. the specular reflection). Higher diffraction orders retain an unknown error term of the form:

$$\frac{A(-k \pm Nk_G)}{A(-k)} \quad (27)$$

In order to eliminate this term, the illumination profile A(k) should be calibrated as discussed below.

The mirror may be a single convex or concave mirror (e.g., mirrors 52b or 52a, respectively, shown in FIGS. 15B and 15A, respectively), or it may be a plane mirror that is actively tilted over a range of angles during detection. Alternatively, there may be a range of mirrors (e.g., element 52c shown in FIG. 15C) at different tilt angles. The measured reflection angle may be in a radial direction (this alters the magnitude of the tilt) or in an azimuthal direction (this alters the direction of the tilt).

The method used to determine the differential equation will now be described in 1-dimension. The extension to 2 dimensions is trivial.

A reference mirror is measured for two small opposite mirror tilts $\pm\theta_M$ of the order of 1 mrad. As a result of this tilt, the measured pupil image will shift. Two slightly shifted images are therefore measured:

$$M_{\pm\theta}(k) = A(-k \pm \Delta(k)) R_M(k) B(k) C(k; \pm\theta) \quad (28)$$

Here, $\Delta$ is the shift in the pupil plane, which generally depends on the position k in the pupil plane. For an aplanatic system:

$$\Delta(k) = 2\theta_M \sqrt{1-k^2} \quad (29)$$

C in equation (28) accounts for the redistribution of the reflected intensity and for an aplanatic system:

$$C(k; \Delta) = 1 + \frac{2\theta_M k}{\sqrt{1-k^2}} \quad (30)$$

$$Q_M(k) = \frac{M_{+\theta} - M_{-\theta}}{M_{+\theta} + M_{-\theta}} \quad (31)$$

where $M_{+\theta}$ and $M_{-\theta}$ are spectra measured at a small positive tilt and small negative tilt respectively.

Here, the subscript 'M' of Q is used to emphasize that it concerns measured data. For small tilts, an approximation may be:

$$A(k + \Delta(k)) \cong A(k) + \frac{dA}{dk} \Delta(k) \quad (32)$$

Using this linearization yields for Q the differential equation:

$$\frac{Q(k)}{\Delta(k)} = \frac{1}{A(k)} \frac{dA}{dk} \quad (33)$$

This equation is easily solved to yield:

$$A(k) = \exp\left[\int_0^k \frac{Q(k')}{\Delta(k')} dk'\right] \quad (34)$$

The above derivation can be easily extended to 2 dimensions. In practice, the measured data is not continuous but is digitized sampled data. However, this does not alter the concept derived above.

In practice, a plane mirror (e.g., element 52 shown in FIG. 5) may be employed that is mechanically tilted using actuators (e.g., actuator 51 shown in FIG. 5). A more elegant and simple approach is the use of a concave or convex mirror (e.g., elements 52a and 52b, respectively, shown in FIGS. 15A and 15B, respectively) with a radius of curvature R and lateral position x. The local height z of a curved mirror is described by:

$$z = \frac{x^2}{2R} \quad (35)$$

The local slope of the surface $\theta$ scales linearly with the lateral position x:

$$\theta \cong \frac{dz}{dx} \quad (36)$$
$$= \frac{x}{R}$$

A concave or convex spherical aluminum fiducial on the substrate stage therefore renders the calibration straightforward because the proper tilt is simply achieved by moving the fiducial to the proper location under the detector.

An embodiment of the invention uses a radiation beam with an annular intensity distribution in a conjugate plane to the substrate. In order to create the annular intensity distribution, the radiation source may comprise mechanical blades, spatial light modulators or spatially coherent broadband lasers and a zoom-axicon (i.e. to create a ring of laser light). In an embodiment, the annular radiation beam comprises small-$\Phi$ illumination.

Implementing annular radiation has advantages over, say, inserting a blade, because there is no radiation loss because almost all the photons are "used". This is particularly important where radiation sources such as UV or DUV are used because they emit fewer photons than more abundant radiation sources and so losing a number of those photons is more noticeable. In particular, this is noticeable in signal collection because the lithographic tool suffers a certain amount of delay if there is a lower radiation intensity. Annular radiation sources have a further advantage of not causing internal reflections as blades might. Internal reflections require blocking to avoid radiation artifacts. Of course, other illumination techniques, such as quadrupole illumination, which offer one or more of the same advantages may be used.

Ideally, the annulus of the annular radiation is placed in the pupil plane of the high NA lens. However, the pupil plane is not directly accessible and in practice, the annulus is placed in a back-projected image of the pupil plane in the illumination branch of the scatterometer. An advantage of annular illumination is that the intensity of the +1/−1 diffraction order of a grating with a small pitch of the order of λ/NA may be separately measured.

Figure 9A:
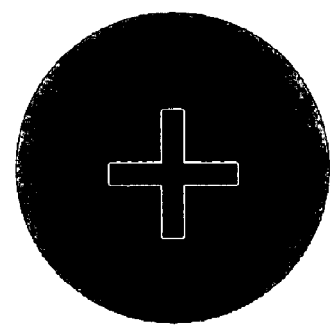
FIGS. 9a and 9b depict a shaped obscuration in an inspection beam according to an embodiment of the invention.
Figure 9B:
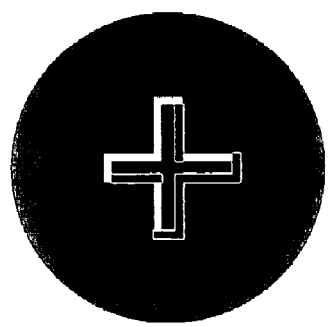

This embodiment may be used for calculating variations in substrate tilt by putting a shaped obscuration in the radiation beam and detecting changes in the width and shape of the shaped obscuration on the substrate caused by variations in the substrate tilt. The shaped obscuration may be, for example, a cross-hair as shown in FIGS. 9a and 9b. It may, of course, be any other shape and it does not have to be in the center of the pupil plane.

The idea of measuring substrate tilt is based on the fundamental relation that a tilt in the substrate plane causes a shift in the pupil plane. In the present embodiment, a cross-haired obscuration is placed in the center of the illumination beam. This produces a black cross-hair in the scattered light in the pupil plane as shown in FIG. 9a.

The location of this cross will vary if the substrate tilt changes. As a result, the difference may be measured between this pattern (at zero tilt) and an actual measurement at an unknown tilt to obtain an image as shown in FIG. 9b. A small tilt in the substrate does not lead to a substantial shape change in the annulus of radiation, but rather, it will lead to a shift of the pupil plane image. This shift is generally small and of the order of 0.1 pixels. In order to be able to detect such a small shift, the values between pixels may be interpolated by curve fitting, for example. By fitting a curve through the dark-light transition that occurs at the edge of the annulus, sub-pixel displacements of the annulus may be measured.

The width and sign of these transitions can be used to calculate and correct for the substrate tilt in 2 dimensions. In this way the substrate can be measured at constant (zero) tilt.

Figure 10:
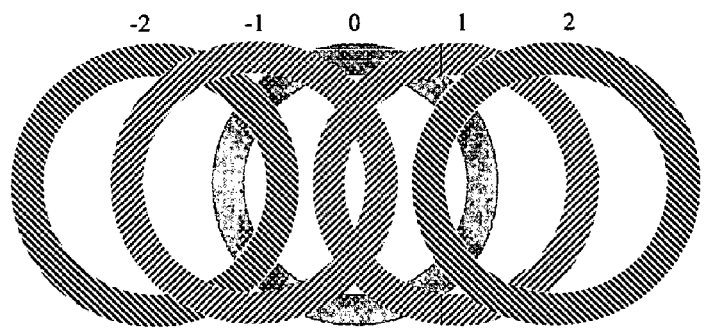
FIG. 10 depicts a detected image of different diffraction orders of scattered spectra according to an embodiment of the invention.

FIG. 10 shows the diffraction orders of small pitched gratings detected using radiation with an annular intensity distribution in a conjugate plane to the substrate. Using an annular intensity distribution allows the shape of the images as shown in FIG. 10 and thereby allows clearer and more precise measurement of substrate tilt. The image labelled 0 is the central zero-order diffraction order as imaged in the detector. The images labelled −2, −1, 1 and 2 are higher diffraction orders. These higher diffraction orders are shifted with respect to the lower diffraction order and so are easier to measure for overlay metrology of isolated 1-D and 2-D features.

In order to speed up calculation times, there are cases in which it may not be necessary to calculate a simulated signal in every single position in the pupil plane, especially when smooth variations are expected. In these cases, a coarse grid may be measured and a pixel interpolation technique used to interpolate the overall shape at the pupil plane. An annular beam is more advantageous in this case, too, because there are areas in the pupil plane that only receive radiation from first order diffraction. If a block beam were used, for instance, each point in the pupil plane would receive radiation from either the zeroth order or a combination of the zeroth order and the first order, causing errors in the measurement at the pupil plane.

Normal measurements using a scatterometer involve measuring the one or more properties of a single target on a single substrate with a single polarization at one time. This may limit the throughput of substrates through the scatterometer, and potentially exposure steps. An embodiment of the invention uses an illumination source to project a plurality of illumination spots onto a substrate. The detector of the scatterometer simultaneously detects an angle-resolved spectrum of the plurality of illumination spots reflected from a surface of the substrate. The plurality of illumination spots may be created using a double illumination fiber or a Wollaston prism to create two orthogonally polarized illumination spots.

Figure 11:
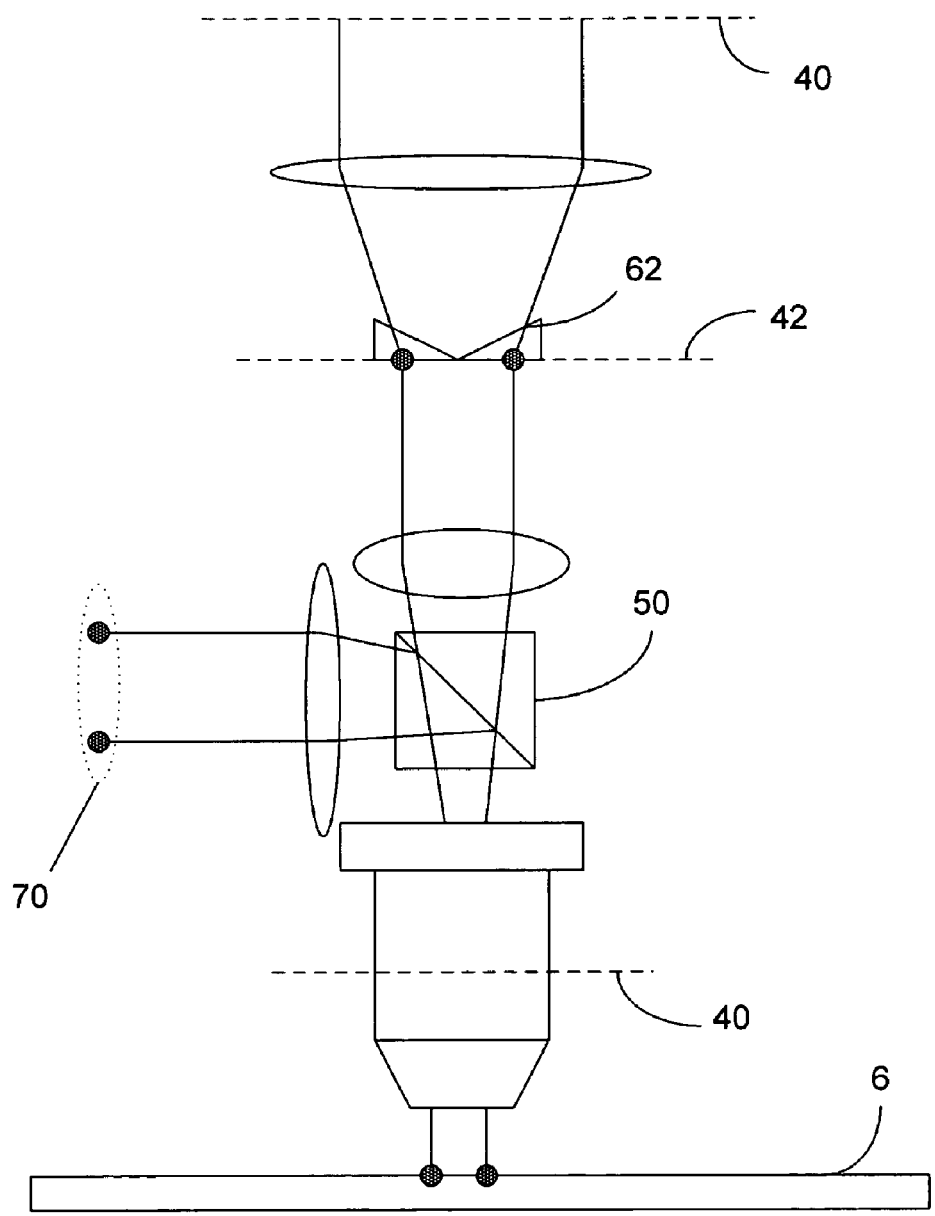
FIG. 11 depicts a scatterometer with two illumination spots according to an embodiment of the invention.

FIG. 11 shows part of the scatterometer hardware. Two illumination spots 70 are split in beam splitter 50 before being transmitted down through the high numerical aperture objective positioned in the pupil plane 40 onto the substrate 6. The reflected beam is transmitted upwards through two wedges 62 that separate the two angle-resolved spectra in the pupil plane, the wedges themselves being positioned in the intermediate image plane 42. The illumination beams are then detected by the CCD on the re-imaged pupil plane 40 at the top of FIG. 11. Two, or even more, parallel measurements may thereby be made—for example, of horizontal and vertical lines for a single polarization or even for both horizontal and vertical lines for both TE and TM polarization.

An embodiment of the invention converts the scatterometer into an ellipsometer. In order to do this, the illumination branch further includes a first polarizer configured to linearly polarize the radiation beam; a beam splitter configured to split the radiation beam into two orthogonal components ($E_{TE}$, $E_{TM}$); a second polarizer configured to polarize the scattered beam; a variable compensator (a Pockells Cell, Wollaston prism pair or Soleil-Babinet compensator) positioned between the first and second polarizers, the variable compensator being configured to vary the optical path difference between orthogonally polarized components (and optionally between the beam splitter and the high numerical aperture lens); and a 2-dimensional detector for detecting sinusoidal intensity variation of the resultant beam components. The compensator is most commonly in the main illumination branch of the scatterometer, though it may of course be in a second illumination branch. The 2-dimensional detector, such as a Complementary Metal Oxide Semiconductor detector (CMOS), has a high frame rate, i.e. in the region of 1000 frames per second.

Figure 12:
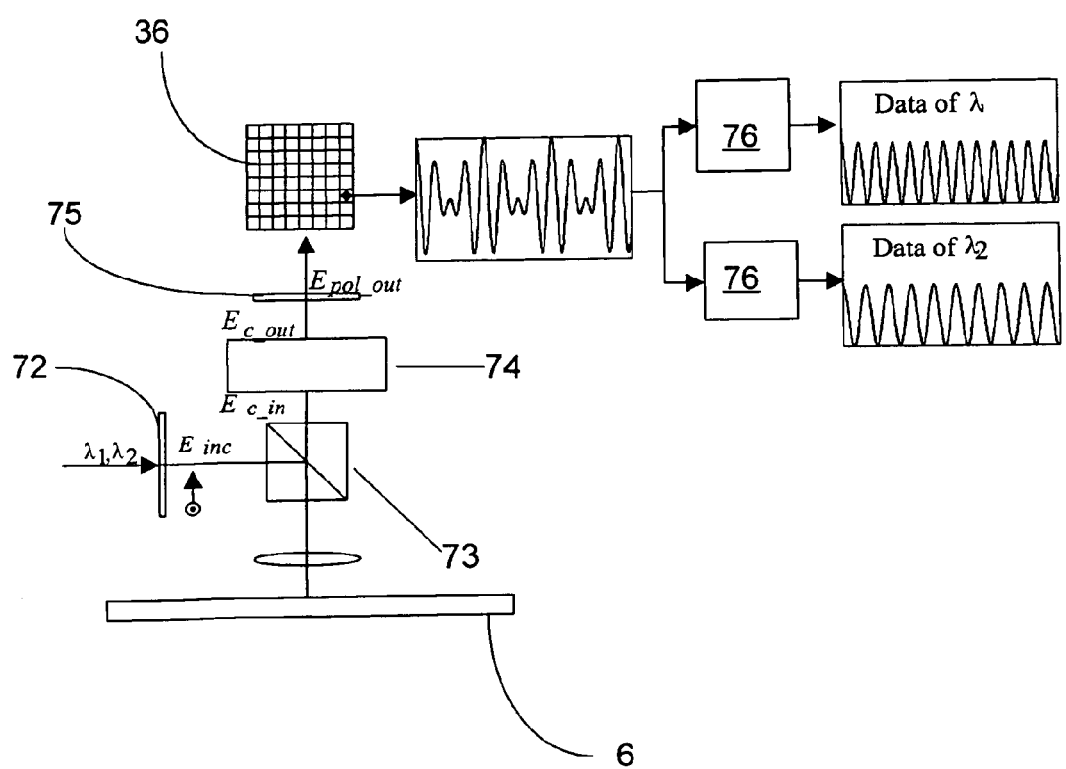
FIG. 12 depicts an ellipsometer according to an embodiment of the present invention.

FIG. 12 shows how the angular-resolved spectroscopic concept is turned into an angle-resolved spectroscopic ellipsometer. An illumination beam with two wavelengths, $\lambda_1$, and $\lambda_2$ is transmitted through a 45° polarizer 72, reflected off the substrate 6 and transmitted through a variable compensator 74 before being polarized again by a 45° polarizer 75. Between the beam splitter 73 and the variable compensator 74, the illumination beam is divided into two beams with a phase difference Δ between the TE and TM polarized beams. The grid 36 in FIG. 12 shows the 2-D detector array and the time-dependent intensity variation in one pixel of this array. The other pixels will show a comparable variation. The beams are passed through two bandpass filters 76 to obtain the illumination profiles of $\lambda_1$ and $\lambda_2$. The resultant ellipsometric parameters $\cos(\Delta)$, $\sin(\Delta)$ and $\tan(\Psi)$ are virtually insensitive to internal sensor scattering and so the signal to noise ratio can be improved. The operation is modeled with Jones vectors and matrices below, though it could also be modeled using Mueller matrices, which enable the inclusion of imperfections of the optical components in the mathematical models.

The illumination field after the first polarizer is 45° polarized and described by the Jones vector:

$$E_{inc} = \begin{bmatrix} 1 \\ 1 \end{bmatrix} \tag{37}$$

Basis vectors correspond to TE and TM polarized radiation that is incident on a target on a sample. The act of reflecting off the sample causes an alteration in the amplitude and the phase of the scattered TE and TM components. This can be represented by a Jones matrix:

$$J_{sample} = \begin{bmatrix} R_{TE} & 0 \\ 0 & R_{TM} e^{j\Delta} \end{bmatrix} \tag{38}$$

where Δ is the phase difference between the TE and TM components of the scattered fields and $R_{TE}$ and $R_{TM}$ are the amplitudes of, respectively, the scattered TE and TM fields.

These parameters are a function of angle of incidence and wavelength. Ignoring any phase and amplitude variations introduced by the high-NA lens and the beam splitter, for the incident field on the compensator:

$$E_{c\_in} = J_{sample} E_{inc} \tag{39}$$

$$= \begin{bmatrix} R_{TE} \\ R_{TM} e^{j\Delta} \end{bmatrix}$$

The compensator introduces a time-varying optical path difference (OPD) variation between the TE and TM components. If the wavelength of the radiation is $\lambda$, for the Jones matrix of the compensator:

$$J_{comp} = \begin{bmatrix} 1 & 0 \\ 0 & e^{j2\pi \frac{OPD(t)}{\lambda}} \end{bmatrix} \quad (40)$$

and so the field after the compensator is:

$$E_{c\_out} = J_{comp} E_{c\_in} \quad (41)$$

$$= \begin{bmatrix} R_{TE} \\ R_{TM} e^{j\left(\Delta + 2\pi \frac{OPD(t)}{\lambda}\right)} \end{bmatrix}$$

The second polarizer is oriented at 45° and has a Jones matrix:

$$J_{pol} = \frac{1}{2} \begin{bmatrix} 1 & 1 \\ 1 & 1 \end{bmatrix} \quad (42)$$

and so the field after the second polarizer is:

$$E_{pol\_out} = J_{pol} E_{c\_out} \quad (43)$$

$$= \frac{1}{2} \begin{bmatrix} R_{TE} + R_{TM} e^{j\left(\Delta + 2\pi \frac{OPD(t)}{\lambda}\right)} \\ R_{TE} + R_{TM} e^{j\left(\Delta + 2\pi \frac{OPD(t)}{\lambda}\right)} \end{bmatrix}$$

The intensity incident on the detector array is:

$$I_d = E_{pol\_out}^T \cdot E_{pol\_out}^* \quad (44)$$

$$= \frac{1}{2} \left[ R_{TE}^2 + R_{TM}^2 + 2 R_{TE} R_{TM} \cos\left(\Delta + 2\pi \frac{OPD(t)}{\lambda}\right) \right]$$

If the OPD increases linearly over the measurement time interval, OPD=Kt
This yields a time-harmonic intensity variation:

$$I_d = \frac{1}{2} [R_{TE}^2 + R_{TM}^2 + 2 R_{TE} R_{TM} \cos(\Delta + \Omega t)] \quad (45)$$

where $$\Omega = 2\pi \frac{K}{\lambda} \quad (46)$$

The contrast of the intensity variation is directly related to the ellipsometric parameter $\tan(\Psi)$ and the phase of the sinusoidal variation directly yields the ellipsometric parameters $\cos(\Delta)$ and $\sin(\Delta)$. In a standard ellipsometric scatterometer, $\tan(\Psi)$ and $\cos(\Delta)$ are the signals that are measured and simulated to obtain the profile information. In that case, $\tan(\Psi)$ and $\cos(\Delta)$ are recorded as a function of wavelength. In an embodiment of the present invention, $\tan(\Psi)$ and $\cos(\Delta)$ are obtained as a function of position in the pupil plane and can be used for similar analyses. In particular, the ellipsometric parameters are used to measure layer thickness by solving an inverse scattering problem, i.e. the measured parameters are compared with modeled parameters and the stack parameters are determined by minimizing the root-mean-square difference (or any other suitable metric) between the measured and modeled parameters.

Because the frequency of the variation depends on the wavelength, the various wavelengths can be separated with a bandpass filter. This can be easily realized via signal processing with, for example, discrete Fourier Transform techniques.

The compensator may also be placed in the illumination branch. Moreover, it may also be placed between the beam splitter and a high numerical aperture objective. This has the advantage that the OPD variation is doubled.

The 2-D detector is a significant aspect of this concept—to ensure sufficiently short measurement times, it should have a high frame rate. CMOS detectors can achieve very high frame rates, for example 1000 frames per second.

Measuring overlay as described starting at paragraph 52 above may not allow for the measurement of large overlay, in particular, overlay equal to an integer times the grating pitch. Clearly, the ability to detect overlay smaller than the grating pitch is of no use if there is an overlay where the grating lines are lined up with each other, but shifted by several grating pitch widths.

An embodiment of the invention therefore uses a second detector branch already present in the scatterometer (and discussed above) to carry out coarse overlay measurements to determine whether coarse errors exist, such as whether the grating overlay is in fact greater than the pitch of the grating. A coarse overlay measurement is an imaging-based technique, wherein a second camera looks at an image of two overlapping gratings and determines whether there are large displacements by comparing the positions of the edges of markers on a substrate. A perfect overlay will have perfectly aligned marker edges. Pattern recognition algorithms are used to determine the edge of a grating in the process layer and the edge of the grating in the resist layer. This measurement is done on the four sides or corners of a grating pair. The measured edge positions are used to calculate the position of the resist grating relative to the position of the grating in the process layer.

The fact that scatterometry on its own cannot measure overlay that is equal to a multiple number of the grating pitch is a fundamental limitation because the measurement principle is based on grating coupling that varies periodically with the grating pitch. In other words, zero overlay and an overlay equal to the pitch yield identical results.

Figure 13:
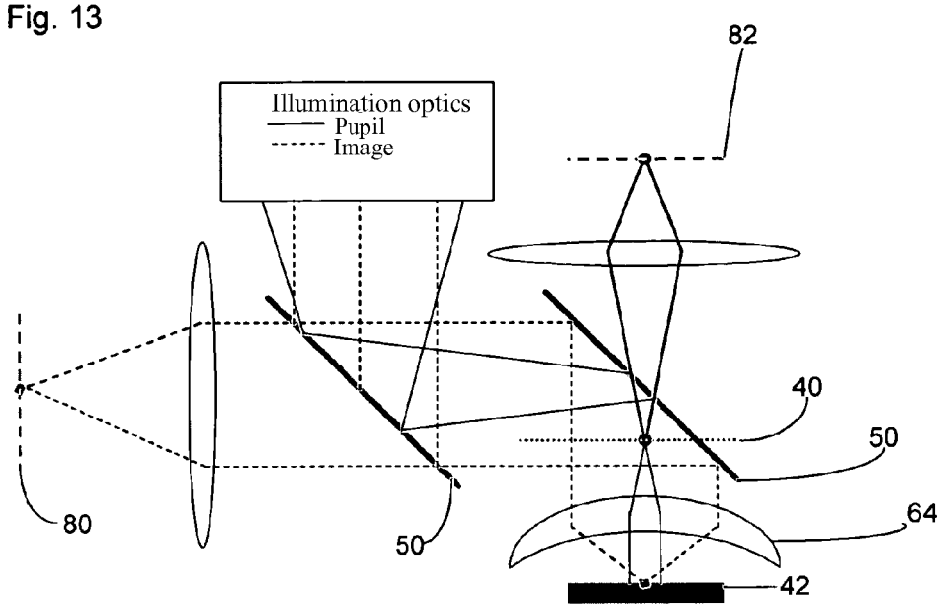
FIG. 13 depicts a scatterometer configured to detect images in the pupil plane and the image plane according to an embodiment of the present invention.

The scatterometer according to an embodiment of the present invention provides a very simple solution. The scatterometer comprises a separate imaging branch that images the substrate surface on a CCD camera. This second camera branch is used to measure the position of the substrate through an alignment and pattern recognition step. The second branch is shown schematically in FIG. 13.

The pupil plane 40 measurement (the actual angle-resolved measurement) requires an illumination source that underfills the target at the object plane 42 (i.e. the measurement spot is smaller than the measurement target). The pupil plane imaging illumination beams are shown as solid lines in FIG. 13. In this case, only a portion of the target is measured and structures outside the target area are not illuminated. If the measurement spot fills or overfills the measurement target, the measurement signal is disturbed by the area surrounding the target and data interpretation and signal analysis are unnecessarily complicated.

The image plane measurement, on the other hand, must overfill the target in order to detect the alignment because the complete pupil plane must be sampled, including the contours of the target. The rays for the image plane measurements are shown as dashed lines. The image of the object plane is formed on a first CCD camera 80 and the image of the pupil plane is formed on a second CCD camera 82.

Figure 14:
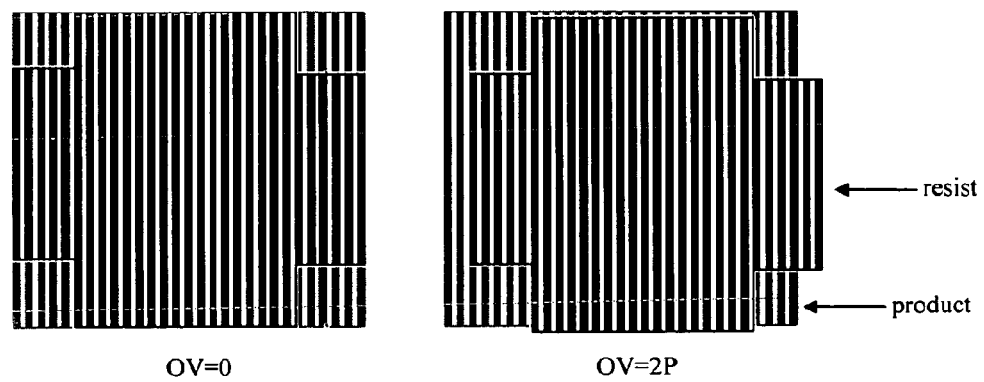
FIG. 14 depicts a grating overlay of twice the pitch of a grating.

FIG. 14 shows one possible example of an overlay target for zero overlay (left-hand drawing) and an X-overlay equal to twice the grating pitch (right-hand drawing). The pupil plane measurement would yield the same measured overlay of zero for both situations making it an unreliable measurement. The image plane measurement, however, can clearly distinguish between these two situations. In this way, a robust two-stage metrology scheme may be carried out as follows:

(1) Two image plane measurements are carried out to verify that there is no large overlay present.

(2) if the previous measurement indicates that overlay is less than approximately 200 nm, the pupil plane measurements are carried out.

The 200 nm criterion is an indicative example. It may be made to any sensible threshold. Assuming that the image plane CCD has 1000×1000 pixels and assuming a pixel pitch of 100 nm at substrate level, the total field of view will be 100×100 $\mu m^2$, which is adequate for pattern recognition and alignment while still allowing coarse overlay measurements with an accuracy of the order of 20-50 nm.

Coarse overlay can only be measured when the entire alignment marker is visible to the CCD. If, for example, only the center part of the marker is visible, the substrate table needs to be moved to the edge of the marker to enable the measurement of the coarse overlay. This calls for additional movement of the table, thereby slowing the measurement taking process. A larger field of view allows the capture of the marker in one "stroke" and a coarse measurement to be carried out quickly while a second camera is free to capture the image on the pupil plane and obtain the detailed overlay information.

The field of view for capturing the relevant image can be reduced even further if the results of edge pre-alignment and coarse substrate align in the exposure tool are used. With these data, it is possible to predict the location of the markers on the substrate with $\mu m$ accuracy after the edge pre-alignment in the overlay metrology module is complete.

An embodiment of the invention detects not just overlay, but may detect damaged gratings using a scatterometer arranged for CD metrology on gratings or other periodic structures. The scatterometer normally detects specular radiation, i.e. lowest order radiation that has been reflected directly off the grating. Local distortions in the grating destroy the periodicity of the grating and result in scattering in a non-specular direction. The scatterometer can be used to detect an angle-resolved spectrum of the scattered beam at various angles outside its specular direction. Radiation with an annular intensity distribution, or small-$\Phi$ illumination, may be used for greater accuracy and images that easier to read.

An embodiment of the invention may be used to detect bubble defects in an immersion lithographic apparatus, where a liquid is introduced between the projection system and the substrate as discussed above. Previously, bubble defects have been measured using an off-line defect inspection tool. Off-line tools take a longer time to produce results than on-line tools because substrates must be taken out of the production line and queued. Bubbles in the liquid cause a surface imperfection on the substrate, which will cause radiation scattering when the surface is exposed to radiation. This scattered radiation is measured using a scatterometer according to an embodiment of the invention and the cause of the scattering may be extrapolated back to bubble defects.

While specific embodiments of the invention have been described above, it will be appreciated that the invention may be practiced otherwise than as described. The description is not intended to limit the invention. The specifically described embodiments are extensions to a general operating principle and are not necessarily mutually exclusive; they are all combinable in a single metrology tool to increase its effectiveness based on results seen at a detector as described above. Further, although the embodiments described herein relate to lithography applications, the hardware and applications are not limited to these. They may be used for other applications such as monitoring etch process steps and the like.

What is claimed is:

1. A method, comprising:
    directing a radiation beam from a radiation source toward a pattern formed on a substrate;
    splitting the radiation beam into two polarized beam components;
    detecting an angle-resolved spectrum of the two polarized beam components reflected from a surface of the substrate; and
    measuring a property of the substrate by measuring asymmetries between intensities of corresponding diffraction orders diffracted from the pattern in the reflected angle-resolved spectrum,
    wherein the asymmetries are related to an extent of an overlay between two misaligned periodic structures.

2. The method of claim 1, further comprising:
    measuring at least one of:
        an intensity of transverse magnetic and transverse electric polarized light; and
        a phase difference between the transverse magnetic and the transverse electric polarized light.

3. The method of claim 1, further comprising:
    measuring, in the pupil plane of a lens, another property of the reflected angle-resolved spectrum at a plurality of wavelengths substantially simultaneously.

4. The method of claim 1, further comprising:
    directing a portion a portion of the radiation beam for separate measurement.

5. A method, comprising:
    directing a radiation beam from a radiation source toward a pattern formed on a substrate;
    detecting an angle-resolved spectrum of the radiation source reflected from a surface of the substrate;
    measuring a property of the substrate by measuring, at a plurality of wavelengths of the radiation beam, asymmetries between intensities of corresponding diffraction orders diffracted from the pattern in the reflected angle-resolved spectrum; and
    measuring in the pupil plane of a lens, another property of the reflected angle-resolved spectrum at the plurality of wavelengths substantially simultaneously;
    wherein the asymmetries are related to an extent of an overlay between two misaligned periodic structures.

6. The method of claim 5, further comprising:
    measuring at least one of:
        an intensity of transverse magnetic and transverse electric polarized light; and
        a phase difference between the transverse magnetic and the transverse electric polarized light.

7. The method of claim 5, further comprising:
directing a portion of the radiation beam for separate measurement.

* * * * *